United States Patent
Sayeh

(10) Patent No.: US 8,027,715 B2
(45) Date of Patent: Sep. 27, 2011

(54) NON-LINEAR CORRELATION MODELS FOR INTERNAL TARGET MOVEMENT

(75) Inventor: Sohail Sayeh, San Ramon, CA (US)

(73) Assignee: Accuray Incorporated, Sunnyvale, CA (US)

(*) Notice: Subject to any disclaimer, the term of this patent is extended or adjusted under 35 U.S.C. 154(b) by 989 days.

(21) Appl. No.: 11/239,789

(22) Filed: Sep. 29, 2005

(65) Prior Publication Data

US 2006/0074299 A1    Apr. 6, 2006

Related U.S. Application Data

(60) Provisional application No. 60/615,008, filed on Oct. 2, 2004.

(51) Int. Cl.
*A61B 6/00* (2006.01)
*A61N 5/00* (2006.01)

(52) U.S. Cl. .................. 600/426; 600/427; 378/69

(58) Field of Classification Search .......... 600/411, 600/413, 426–428, 429; 606/130; 378/62, 378/69, 205; 702/188
See application file for complete search history.

(56) References Cited

U.S. PATENT DOCUMENTS

| | | | |
|---|---|---|---|
| 5,251,128 A * | 10/1993 | Crawford ................ 600/425 |
| 5,287,276 A | 2/1994 | Crawford et al. |
| 5,538,494 A | 7/1996 | Matsuda |
| 5,727,554 A * | 3/1998 | Kalend et al. .......... 600/587 |
| 5,764,723 A | 6/1998 | Weinberger |
| 6,076,005 A * | 6/2000 | Sontag et al. ........... 600/413 |
| 6,144,875 A * | 11/2000 | Schweikard et al. ...... 600/427 |
| 6,307,914 B1 | 10/2001 | Kunieda et al. |
| 6,314,312 B1 * | 11/2001 | Wessels et al. .......... 600/427 |
| 6,341,179 B1 | 1/2002 | Stoyle et al. |
| 6,385,286 B1 | 5/2002 | Fitchard |
| 6,468,265 B1 | 10/2002 | Evans et al. |
| 6,501,981 B1 * | 12/2002 | Schweikard et al. ...... 600/427 |
| 6,662,036 B2 * | 12/2003 | Cosman ................. 600/411 |
| 6,690,965 B1 * | 2/2004 | Riaziat et al. ........... 600/428 |
| 6,704,691 B2 | 3/2004 | Chiou |
| 6,731,970 B2 | 5/2004 | Schlossbauer |
| 6,778,850 B1 | 8/2004 | Adler |
| 6,804,548 B2 | 10/2004 | Takahashi et al. |
| 6,841,389 B2 * | 1/2005 | Novikov et al. .......... 436/95 |
| 6,937,696 B1 | 8/2005 | Mostafavi |
| 6,973,202 B2 * | 12/2005 | Mostafavi .............. 382/103 |
| 7,085,342 B2 | 8/2006 | Younis et al. |
| 7,171,257 B2 * | 1/2007 | Thomson ............... 600/427 |
| 7,237,556 B2 * | 7/2007 | Smothers et al. ......... 128/898 |
| 7,367,955 B2 | 5/2008 | Zhang et al. |
| 7,668,585 B2 * | 2/2010 | Green ................... 600/428 |

(Continued)

FOREIGN PATENT DOCUMENTS

DE    10310127    9/2004

(Continued)

OTHER PUBLICATIONS

PCT Written Opinion of the International Searching Authority, International Application No. PCT/US05/35361, International Filing Date Sep. 30, 2005, 1 pg.

(Continued)

*Primary Examiner* — Francis Jaworski
(74) *Attorney, Agent, or Firm* — Lowenstein Sandler PC

(57) ABSTRACT

A method and apparatus to track non-linear internal target movement based on movement of an external marker.

21 Claims, 18 Drawing Sheets

U.S. PATENT DOCUMENTS

| | | | |
|---|---|---|---|
| 7,778,691 B2* | 8/2010 | Zhang et al. | 600/427 |
| 7,822,176 B2 | 10/2010 | Yi et al. | |
| 2001/0014772 A1 | 8/2001 | Lampotang | |
| 2003/0033120 A1* | 2/2003 | Chiou | 702/188 |
| 2004/0071337 A1 | 4/2004 | Jeung | |
| 2004/0092815 A1 | 5/2004 | Schweikard | |
| 2004/0158146 A1 | 8/2004 | Mate | |
| 2005/0033154 A1* | 2/2005 | deCharms | 600/410 |
| 2005/0080332 A1 | 4/2005 | Shiu et al. | |
| 2006/0074299 A1 | 4/2006 | Sayeh | |
| 2006/0074304 A1 | 4/2006 | Sayeh | |
| 2007/0015991 A1 | 1/2007 | Fu et al. | |
| 2007/0230765 A1 | 10/2007 | Wang et al. | |
| 2007/0244386 A1* | 10/2007 | Steckner et al. | 600/411 |

FOREIGN PATENT DOCUMENTS

| | | |
|---|---|---|
| WO | WO 99/27839 | 6/1999 |
| WO | WO03003796 | 1/2003 |
| WO | WO 2005/030330 A1 | 4/2005 |

OTHER PUBLICATIONS

PCT International Search Report, International Application No. PCT/US05/35361, International Filing Date Sep. 30, 2005, mailed Apr. 4, 2006.

Mu et al., "Multiple Fiducial Identification using the Hidden Markov Model in Image Guided Radiosurgery", 2006 IEEE.

PCT International Preliminary Report on Patentability (Chapter I of the Patent Cooperation Treaty), PCT/US2005/035361 filed Sep. 30, 2005, mailed Apr. 12, 2007.

Coste-Manière, È., "Robotic whole body stereotacitc radiosurgery: clinical advantages of the CyberKnife® integrated system", The International Journal of Medical Robotics +Computer Assisted Sugery, 2005, www.roboticpublications.com, 14 pages.

Accuray Treatment Delivery Manual, Jan. 2007.

European Extended Search Report, EP 05800223.9, dated Mar. 29, 2010, mailed Apr. 7, 2010, 9 pages.

Qin-Sheng Chen et al., "Fluoroscopic study of tumor motion due to breathing: Facilitating precise radiation therapy for lung cancer patients", Med. Phys. 28 (9), Sep. 2001, pp. 1850-1856.

Hiroki Shirato et al., "Intrafractional Tumor Motion: Lung and Liver", Seminars in Radiation Oncology, vol. 14, No. 1 Jan. 2004: pp. 10-18.

U.S. Appl. No. 11/240,593, Final Office Action dated Dec. 8, 2010.

U.S. Appl. No. 11/240,593, Office Action dated Feb. 6, 2008, 25 pages.

U.S. Appl. No. 11/240,593, Office Action dated Sep. 8, 2008, 19 pages.

U.S. Appl. No. 11/240,593, Office Action dated Jun. 22, 2010, 22 pages.

* cited by examiner

Path of Movement (2D)

Movement and Respiration vs. Time

Data Points on Path of Movement

Data Points on Time Scale

Linear Correlation of x-Movement
vs. Movement of External Marker

Linear Correlation of z-Movement
vs. Movement of External Marker

Linear Correlation Model

Nonlinear Correlation of x-Movement
vs. Movement of External Marker

Nonlinear Correlation of z-Movement
vs. Movement of External Marker

Nonlinear Correlation Model

Multi-Poly Correlation of x-Movement
vs. Movement of External Marker

Multi-Poly Correlation of z-Movement
vs. Movement of External Marker

Multi-Poly Correlation Model

Matching Approximations for
Multi-Poly Correlation Model

Multi-Linear Correlation of x-Movement
vs. Movement of External Marker

Multi-Linear Correlation of z-Movement
vs. Movement of External Marker

Multi-Linear Correlation Model

Matching Approximations for
Multi-Linear Correlation Model

NON-LINEAR CORRELATION MODELS FOR INTERNAL TARGET MOVEMENT

RELATED APPLICATIONS

This application claims the benefit of U.S. Provisional Application No. 60/615,008 filed on Oct. 2, 2004.

TECHNICAL FIELD

This invention relates to the field of radiation treatment and, in particular, to tracking target movement in radiation treatment.

BACKGROUND

Pathological anatomies such as tumors and lesions can be treated with an invasive procedure, such as surgery, but can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted.

In many medical applications, it is useful to accurately track the motion of a moving target region in the human anatomy. For example, in radiosurgery, it is useful to accurately locate and track the motion of a target region, due to respiratory and other patient motions during the treatment. Conventional methods and systems have been developed for performing tracking of a target treatment (e.g. radiosurgical treatment) on an internal target, while measuring and/or compensating for breathing and/or other motions of the patient. For example, U.S. Pat. Nos. 6,144,875 and 6,501,981, commonly owned by the assignee of the present application, describe such conventional systems. The SYNCHRONY® system, manufactured by Accuray, Inc., can carry out the methods and systems described in the above applications.

These conventional methods and systems correlate internal organ movement with respiration, using a linear model based on respiration position. However, these conventional technologies do not take into account internal organ movements along different inspiration and expiration paths. Although some internal organs may move along one path during inspiration and along another path during expiration, these conventional technologies do not distinguish these different paths because they consider only the position of the internal organ. In particular, conventional technologies use a linear approach to model the organ movement, despite the disparate inspiration and expiration paths of the internal organ. While the conventional linear modeling may have been an improvement over previous technologies, conventional linear modeling technologies are limited in their ability to model multi-path and other non-linear organ movements.

BRIEF DESCRIPTION OF THE DRAWINGS

The present invention is illustrated by way of example, and not by way of limitation, in the figures of the accompanying drawings.

DETAILED DESCRIPTION

Figure 1:
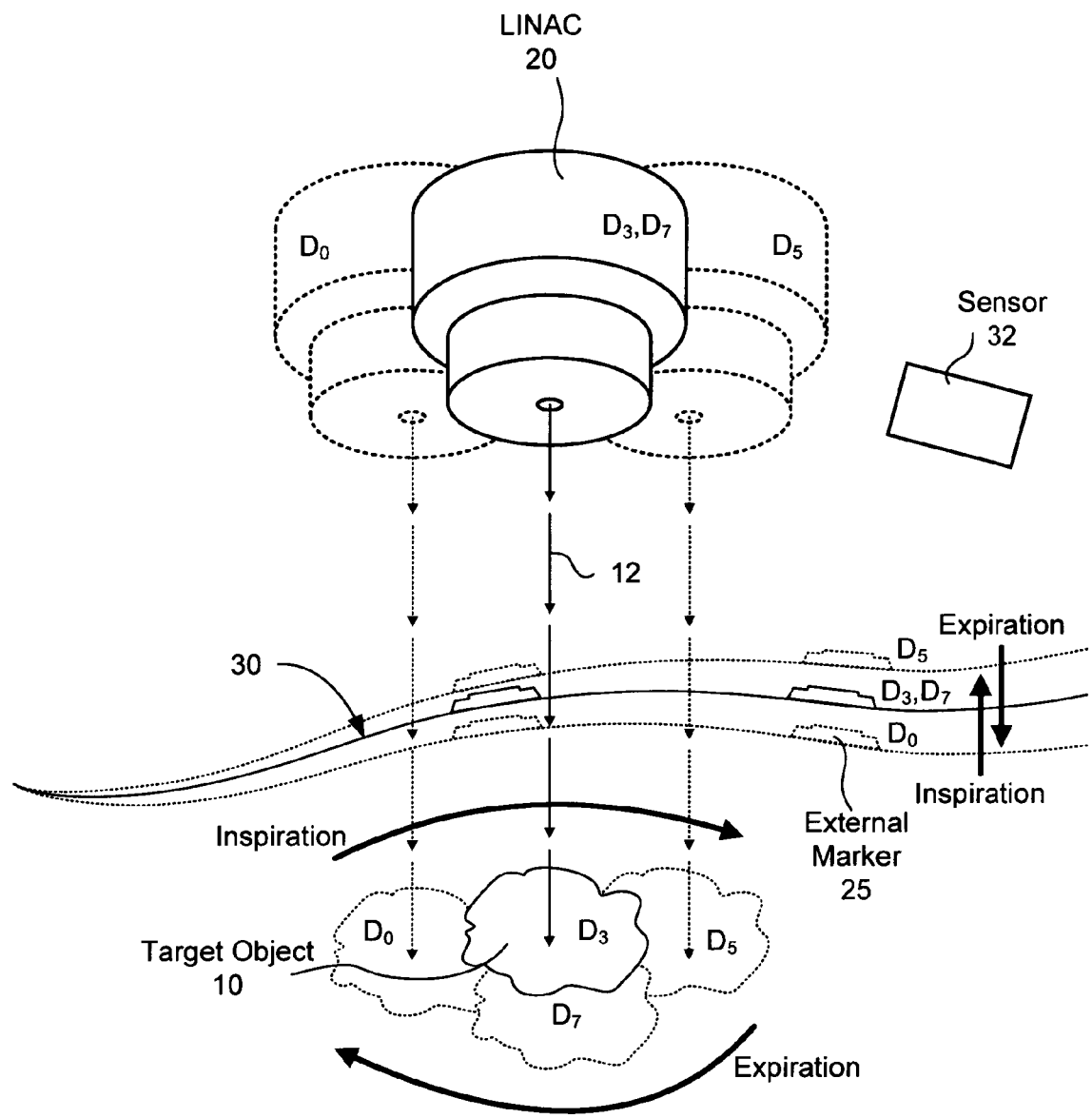
FIG. 1 illustrates a cross-sectional view of a treatment tracking environment.

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of the present invention include various operations, which will be described below. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product which may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage media (e.g., floppy diskette); optical storage media (e.g., CD-ROM); magneto-optical storage media; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of media suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Embodiments of a method and apparatus are described to track internal object movement based on movement of an external marker. In one embodiment, a method and system are presented to identify the correlation between movement(s) of a target such as an internal organ and respiration (or other motion such as heartbeat) of a patient. These movements may include linear movements, non-linear movements, and asymmetric movements. In one embodiment, the method and system may facilitate modeling movement paths of a target that moves along different paths during inspiration and expiration, respectively. One embodiment of the correlation model employs a curvilinear, rather than rectilinear, model to correlate the internal position of the target to respiration.

The method and system may consider position, speed, and/or direction of respiration or the internal object to develop one or more correlation models. The method and system also may use data points in time for which the position of the target is known. Respiration may be monitored in parallel with the monitoring of the target position. Information about the position and the speed/direction of respiration may be obtained at the time of interest. Once established, a correlation model may be used along with a respiration monitoring system to locate and track the internal movement of a target such as an organ, region, lesion, tumor, and so forth.

FIG. 1 illustrates a cross-sectional view of a treatment tracking environment. The treatment tracking environment depicts corresponding movements of an internal target 10 within a patient, a linear accelerator (LINAC) 20, and an external marker 25. The illustrated treatment tracking environment is representative of a patient chest region, for example, or another region of a patient in which an internal organ might move during the respiratory cycle of the patient. In general, the respiratory cycle of a patient will be described in terms of an inspiration interval and an expiration interval, although other designations and/or delineations may be used to describe a respiratory cycle.

In one embodiment, the LINAC 20 moves in one or more dimensions to position and orient itself to deliver a radiation beam 12 to the target 10. Although substantially parallel radiation beams 12 are depicted, the LINAC 20 may move around the patient in multiple dimensions to project radiation beams 12 from several different locations and angles. The LINAC 20 tracks the movement of the target 10 as the patient breathes, for example. One or more external markers 25 are secured to the exterior 30 of the patient in order to monitor the patient's breathing cycle. In one embodiment, the external marker 25 may be a device such as a light source or a metal button attached to a vest worn by the patient. Alternatively, the external marker 25 may be attached to the patient's clothes or skin in another manner.

As the patient breathes, a tracking sensor 32 tracks the location of the external marker 25. For example, the tracking sensor may track upward movement of the external marker 25 during the inspiration interval and downward movement of the external marker 25 during the expiration interval. The relative position of the external marker 25 is correlated with the location of the target organ 10, as described below, so that the LINAC 20 may move relative to the location of the external marker 25 and the correlated location of the target organ 10. In another embodiment, other types of external or internal markers may be used instead of or in addition to the illustrated external marker 25.

As one example, the depicted target 10 is shown in four positions designated as $D_0$, $D_3$, $D_5$, and $D_7$. The first position, $D_0$, may correspond to approximately the beginning of the inspiration interval. The second position, $D_3$, may correspond to a time during the inspiration interval. The third position, $D_5$, may correspond to approximately the end of the inspiration interval and the beginning of the expiration interval. The fourth position, $D_7$, may correspond to a time during the expiration interval. Additional positions of the target 10 on the path of movement are graphically shown and described in more detail with reference to the following figures. As the patient breathes, the target 10 may move along a path within the patient's body. In one embodiment, the path of the target 10 is asymmetric in that the target 10 travels along different paths during the inspiration and expiration intervals. In another embodiment, the path of the target 10 is at least partially non-linear. The path of the target 10 may be influenced by the size and shape of the target 10, organs and tissues surrounding the target 10, the depth or shallowness of the patient's breathing, and so forth.

Similarly, the external marker 25 is shown in a first position, $D_0$, a second position, $D_3$, a third position, $D_5$, and a fourth position, $D_7$, which correspond to the positions of the target 10. By correlating the positions of the external marker 25 to the target 10, the position of the target 10 may be derived from the position of the external marker 25 even though the external marker 25 may travel in a direction or along a path that is substantially different from the path and direction of the target object 10. The LINAC 20 is also shown in a first position, $D_0$, a second position, $D_3$, a third position, $D_5$, and a fourth position, $D_7$, which also correspond to the positions of the target 10. In this way, the movements of the LINAC 20 may be substantially synchronized to the movements of the target 10 as the position of the target 10 is correlated to the sensed position of the external marker 25.

Figure 2:
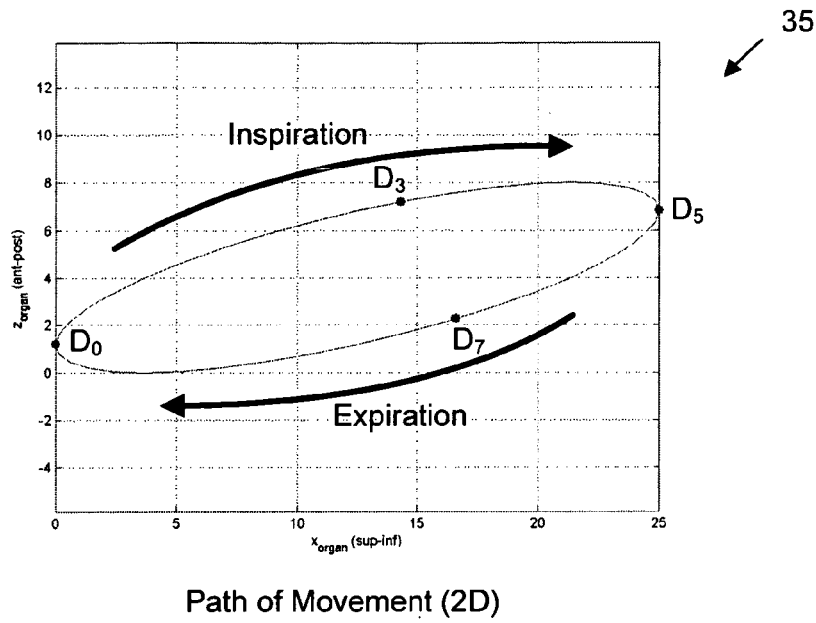
FIG. 2 is a graphical representation of an exemplary two-dimensional path of movement of an internal target during a respiration period.

FIG. 2 is a graphical representation 35 of an exemplary two-dimensional path of movement of an internal target 10 during a respiration period. The horizontal axis represents displacement (e.g., in millimeters) of the target 10 in a first dimension (x). The vertical axis represents displacement (e.g., in millimeters) of the target 10 in a second dimension (z). The target 10 may similarly move in a third dimension (y). As shown in the graph 35, the path of movement of the target 10 is non-linear. Additionally, the path of movement is different during an inspiration period and an expiration period. As an example, the inspiration path may correspond to the upper portion of the graph 35 between zero and twenty-five in the x direction, with zero being a starting reference position, $D_0$, and twenty-five being the maximum displacement position, $D_5$, at the moment between inspiration and expiration. The corresponding expiration period may be the lower portion of the graph 35 between $D_5$ and $D_0$. In the depicted embodiment, the displacement position $D_3$ is on the inspiration path roughly between $D_0$ and $D_5$. Similarly, the displacement position $D_7$ is on the expiration path roughly between $D_5$ and $D_0$. These displacement points are shown with additional displacement points in FIG. 4.

Figure 3:
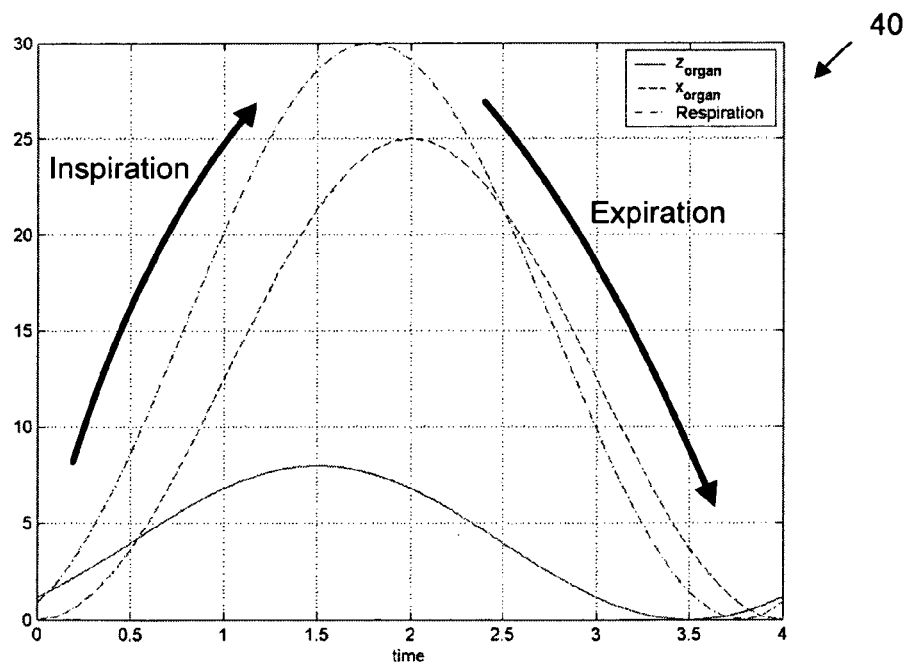
FIG. 3 is a graphical representation of an exemplary path of movement of an internal target during a respiration period, as a function of time.

FIG. 3 is a graphical representation 40 of an exemplary path of movement of an internal target 10 during a respiration period, as a function of time. The graph 40 shows the displacement (e.g., in millimeters) of the target 10 over time (e.g., in seconds) in the x direction (dashed line) and in the z direction (solid line). The graph 40 also shows the displacement (in millimeters) of, for example, an external marker 10 to identify the respiration period (dashed line). In the depicted embodiment, the external marker 25 is maximally displaced (approximately 30 mm) more than the target organ 10 in the x direction (approximately 25 mm) or in the z direction (approximately 8 mm). However, the maximum displacement of the target organ 10 in the various directions does not necessarily align with the maximum displacement of the external marker 25 associated with the respiratory period. Additionally, the maximum displacement of the target organ 10 in the one direction does not necessarily align with the maximum displacement in another direction. For example, the maximum displacement of the external marker 25 occur at approximately 1.75 s, while the maximum displacement of the internal organ 10 in the x and z directions may occur at approximately 2.0 and 1.5 seconds, respectively. These misalignments may be present in both the inspiration and expiration paths.

Figure 4:
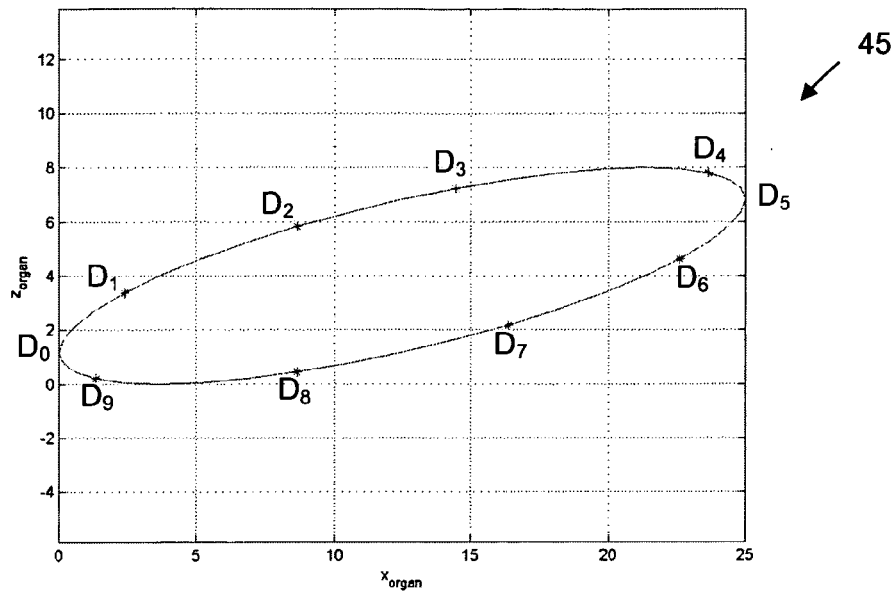
FIG. 4 is a graphical representation of an exemplary set of data points associated with the path of movement shown in FIG. 2.

FIG. 4 is a graphical representation 45 of an exemplary set of data points $D_0$-$D_9$ associated with the path of movement shown in FIG. 2. In particular, the data points $D_0$-$D_9$ are superimposed on the path of movement of the target 10. The data points $D_0$-$D_9$ correspond to various points in time during the respiration period. In the illustrated embodiment, one data point data point $D_0$ designates the initial reference location of the target 10 prior to the inspiration interval. Four data points $D_1$-$D_4$ designate the movement of the target 10 during the inspiration interval. The data point $D_5$ designates the moment between the inspiration and expiration intervals. The data points $D_6$-$D_9$ designate the movement of the target 10 during the expiration interval. The following table provides approximate coordinates for each of the data points $D_0$-$D_9$. Similar coordinates may be provided for the displacement of the external marker 25 or the displacement of the target 10 in another direction.

TABLE 1

| Data Point Coordinates. | |
|---|---|
| Data Point | (x, z) (mm) |
| $D_0$ | (0, 1) |
| $D_1$ | (2, 3) |
| $D_2$ | (8, 5) |
| $D_3$ | (14, 7) |
| $D_4$ | (24, 8) |
| $D_5$ | (25, 7) |
| $D_6$ | (23, 5) |
| $D_7$ | (16, 2) |
| $D_8$ | (8, 0) |
| $D_9$ | (1, 0) |

Figure 5:
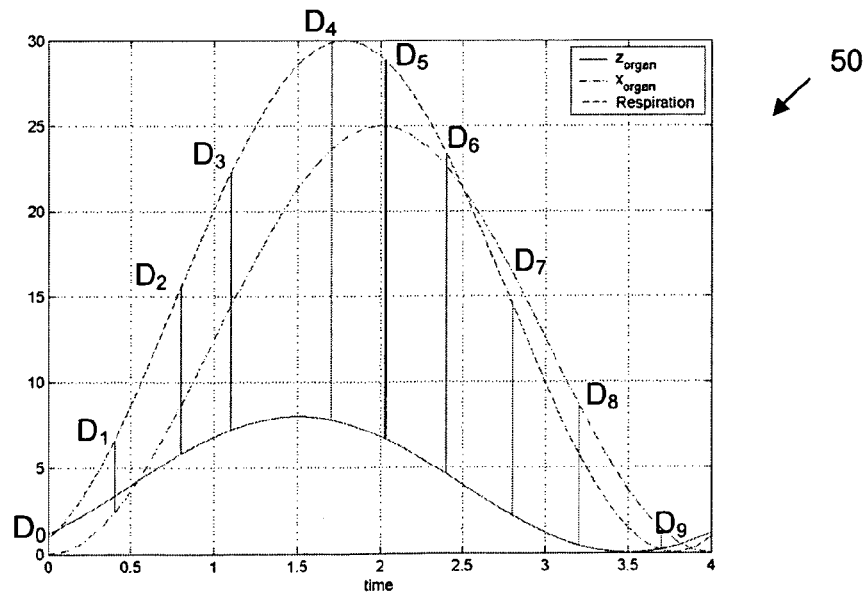
FIG. 5 is a graphical representation of an exemplary set of data points associated with the path of movement shown in FIG. 3.

FIG. 5 is a graphical representation 50 of the exemplary set of data points $D_0$-$D_9$ associated with the paths of movement shown in FIG. 3. The data points $D_0$-$D_9$ are represented by vertical lines superimposed on the path of movement of the target 10 and the external marker 25. The following table provides approximate times corresponding to each of the data points $D_0$-$D_g$, as well as approximate displacement values, r, for the external marker 25.

TABLE 2

Data Point Times.

| Data Point | Time (s) | r (mm) |
| --- | --- | --- |
| $D_0$ | 0.0 | 1 |
| $D_1$ | 0.4 | 6 |
| $D_2$ | 0.8 | 16 |
| $D_3$ | 1.1 | 22 |
| $D_4$ | 17 | 30 |
| $D_5$ | 2.4 | 28 |
| $D_6$ | 2.8 | 23 |
| $D_7$ | 3.2 | 14 |
| $D_8$ | 3.7 | 5 |
| $D_9$ | 4.0 | 0 |

Figure 6:
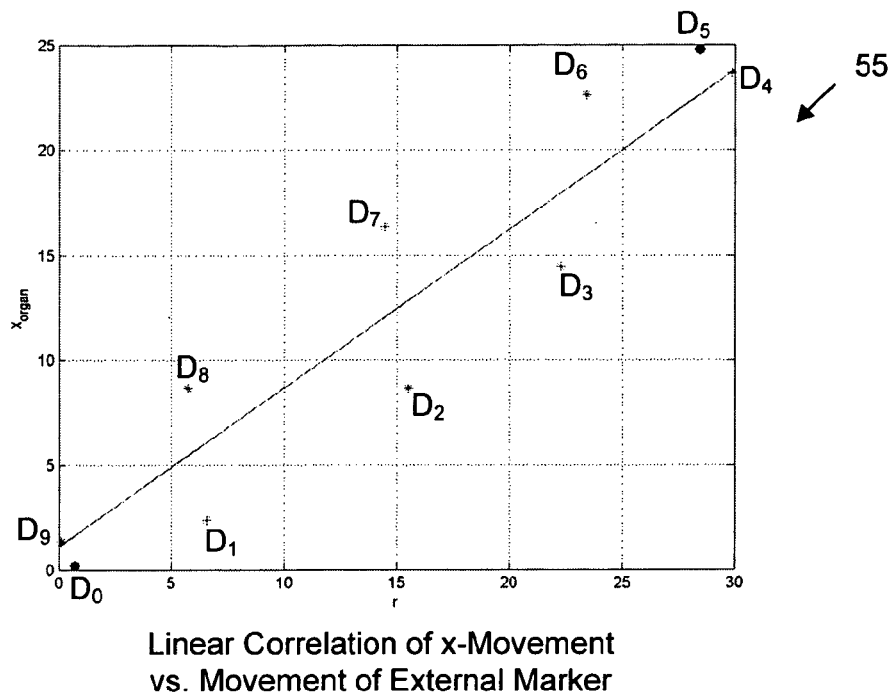
FIG. 6 is a graphical representation of an exemplary least square fit linear correlation model of the path of movement in a first dimension, as a function of movement of an external marker.

FIG. 6 is a graphical representation 55 of an exemplary least square fit linear correlation model of the path of movement in a first dimension, as a function of the displacement, r, of an external marker 10. In particular, the graph 55 shows the (r,x) coordinates from the data points $D_0$-$D_9$ above and superimposes a linear correlation model (dashed line). The following table provides approximate (r,x) coordinates corresponding to each of the data points $D_0$-$D_9$.

TABLE 3

Data Point Coordinates.

| Data Point | (r, x) (mm) |
| --- | --- |
| $D_0$ | (1, 0) |
| $D_1$ | (6, 2) |
| $D_2$ | (16, 8) |
| $D_3$ | (22, 14) |
| $D_4$ | (30, 24) |
| $D_5$ | (28, 25) |
| $D_6$ | (23, 23) |
| $D_7$ | (14, 16) |
| $D_8$ | (5, 8) |
| $D_9$ | (0, 1) |

The linear correlation model may be used to estimate the x displacement of the target 10 based on the respiration displacement, r, measured by the external marker 25. The following equation is exemplary of a linear correlation model that may be employed in conventional linear modeling systems:

$$\begin{Bmatrix} x_{organ} \\ y_{organ} \\ z_{organ} \end{Bmatrix} = \begin{Bmatrix} A_x \\ A_y \\ A_z \end{Bmatrix} r + \begin{Bmatrix} B_x \\ B_y \\ B_z \end{Bmatrix}$$

which may be written in a more compact form as follows:

$$x = ar + b$$

Figure 7:
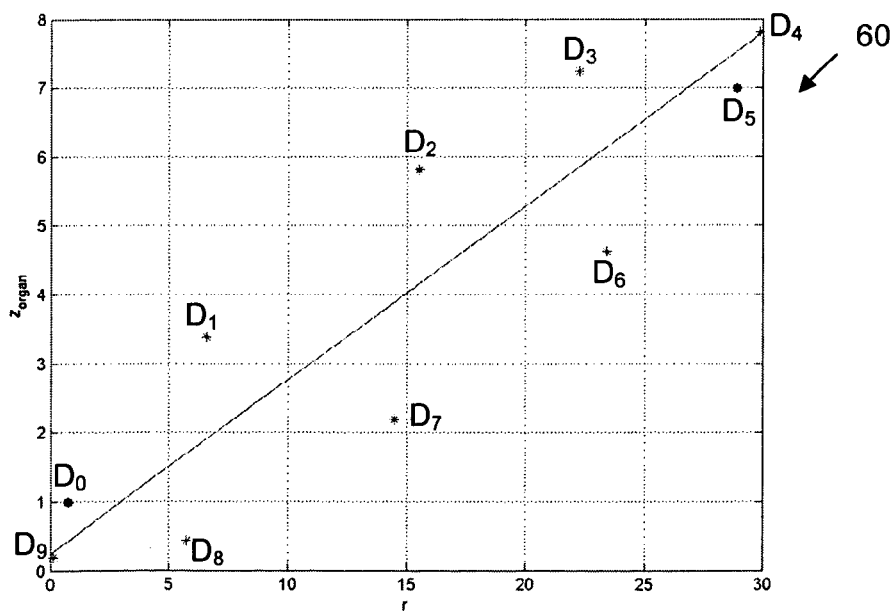
FIG. 7 is graphical representation of an exemplary least square fit linear correlation model of the path of movement in a second dimension, as a function of movement of an external marker.

FIG. 7 is a graphical representation 60 of an exemplary least square fit linear correlation model of the path of movement in a second dimension, as a function of the displacement, r, of an external marker 10. In particular, the graph 60 shows the (r,z) coordinates from the data points $D_0$-$D_9$ above and superimposes a linear correlation model (dashed line). The following table provides approximate (r,z) coordinates corresponding to each of the data points $D_0$-$D_9$. The linear correlation model may be used to estimate the z displacement of the target 10 based on the respiration displacement, r, measured by the external marker 25.

TABLE 4

Data Point Coordinates.

| Data Point | (r, z) (mm) |
| --- | --- |
| $D_0$ | (1, 1) |
| $D_1$ | (6, 3) |
| $D_2$ | (16, 5) |
| $D_3$ | (22, 7) |
| $D_4$ | (30, 8) |
| $D_5$ | (28, 7) |
| $D_6$ | (23, 5) |
| $D_7$ | (14, 2) |
| $D_8$ | (5, 0) |
| $D_9$ | (0, 0) |

Figure 8:
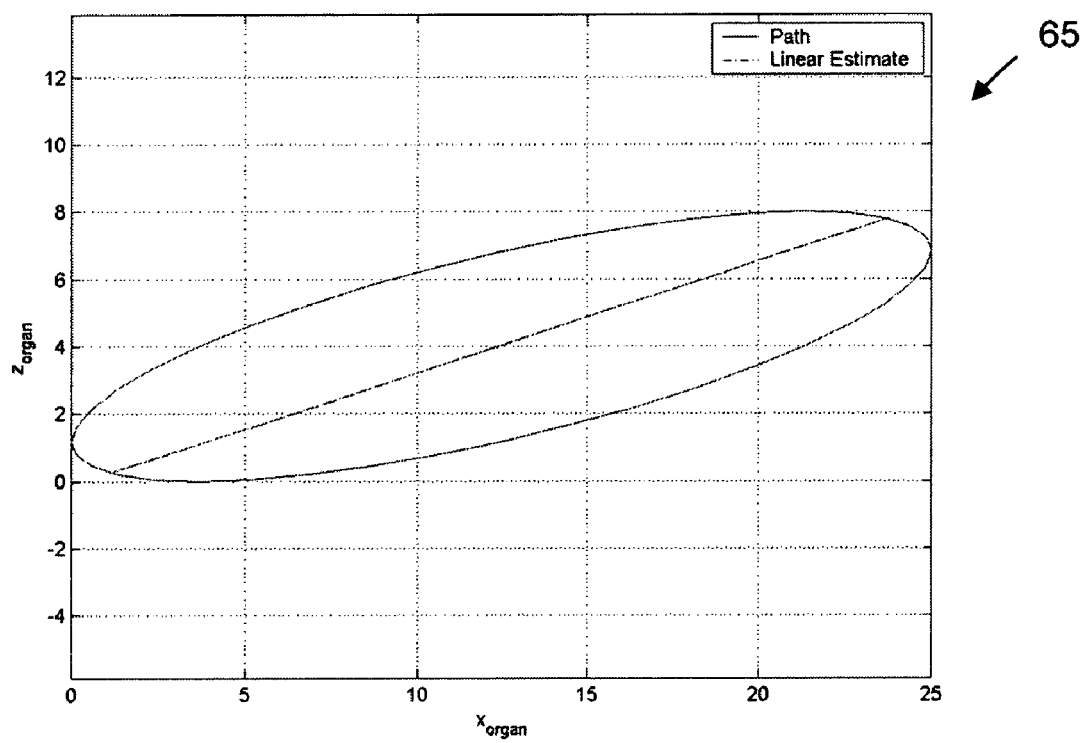
FIG. 8 is a graphical representation of an exemplary estimated path for a linear correlation model in two dimensions.

FIG. 8 is a graphical representation 65 of an exemplary estimated path for a linear correlation model. The graph 65 superimposes the linear correlation model for the x and z directions on the path of movement, shown in FIG. 2, of the target 10. While the linear correlation model is fairly accurate at about (x,z)=(2,0) and (x,z)=(23,8), the linear correlation model has relatively large estimation errors for all of the other coordinates along the path of movement. The estimation error corresponding to the x direction may be determined by the vertical difference (e.g., in millimeters) between the linear correlation model and either the inspiration path (e.g., upper portion) or the expiration path (e.g., lower portion). Similarly, the estimation error for the z direction may be determined by the horizontal difference (e.g., in millimeters) between the linear correlation model and either the inspiration path (e.g., upper portion) or the expiration path (e.g., lower portion). The estimation errors are shown and described in more detail with reference to FIG. 20.

Figure 9:
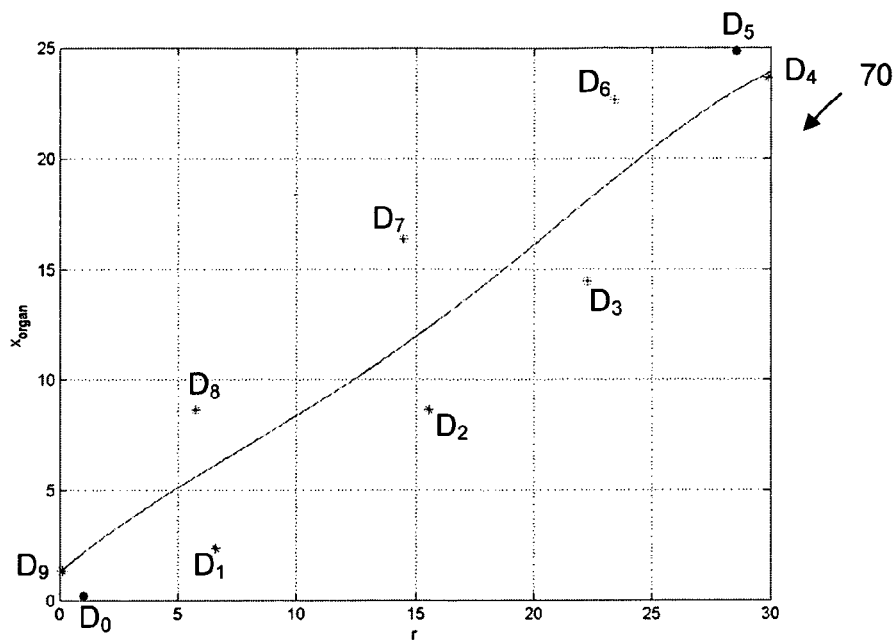
FIG. 9 is a graphical representation of an exemplary non-linear correlation model of the path of movement in a first dimension, as a function of movement of an external marker.

FIG. 9 is a graphical representation 70 of an exemplary nonlinear correlation model of the path of movement in a first dimension, as a function of the displacement, r, of an external marker 10. In particular, the graph 70 shows the (r,x) coordinates from the data points $D_0$-$D_9$ above and superimposes a nonlinear correlation model (dashed line). The approximate (r,x) coordinates corresponding to each of the data points $D_0$-$D_9$ is provided in Table 3 above.

The nonlinear correlation model may be used to estimate the x displacement of the target 10 based on the respiration displacement, r, measured by the external marker 25. The following equation is exemplary of a nonlinear correlation model:

$$x = f(r)$$

where f(r) describes the curve and may be selected depending on the shape of the path of movement of the target 10. In a more particular embodiment, a third order polynomial may be selected as an example of the vector function f(r) of the equation above. In one embodiment, the resulting polynomial curve may be described according to the following equation:

$$x = \sum_{n=0}^{3} a_n r^n$$

In another embodiment, the speed of the respiratory motion (i.e., the derivative of the respiration displacement, r) may be used to build a nonlinear correlation model, as illustrated, that more closely approximates the organ path. For example, using the speed of the external marker 25 may be useful in cases in which the target 10 takes different paths during the inspiration and expiration intervals, respectively, of the respiration period. In other embodiments, the displacement and/or speed of other motions, other than respiration, may be used in addition to or instead of the respiration. One example of an equation that takes into account both displacement, r, and speed, $\dot{r}$, as a second independent variable, is as follows:

$$x = f(r, \dot{r})$$

Figure 10:
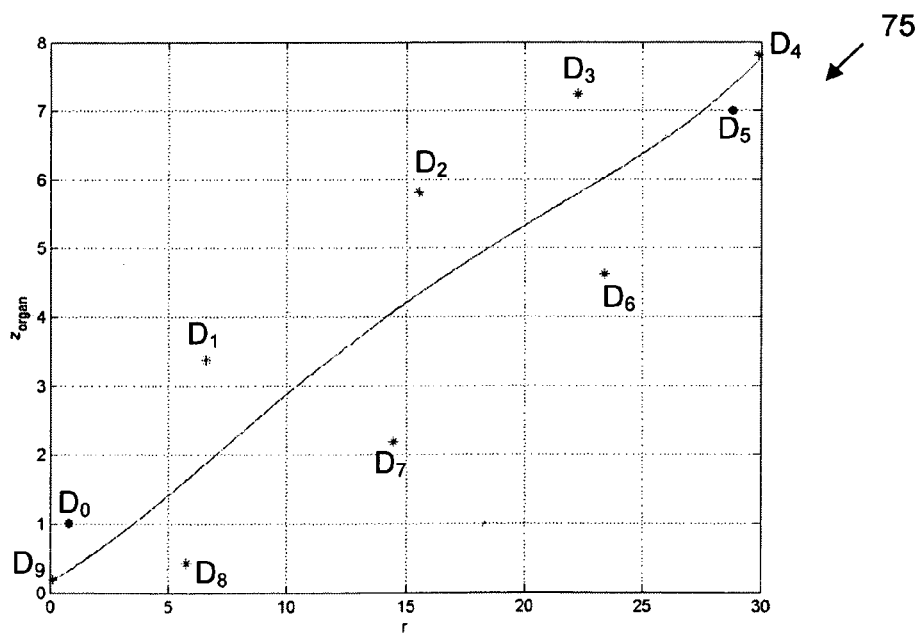
FIG. 10 is a graphical representation of an exemplary non-linear correlation model of the path of movement in a second dimension, as a function of movement of an external marker.

FIG. 10 is a graphical representation 75 of an exemplary nonlinear correlation model of the path of movement in a second dimension, as a function of the displacement, r, of an external marker 10. In particular, the graph 75 shows the (r,z) coordinates from the data points $D_0$-$D_9$ above and superimposes a nonlinear correlation model (dashed line). The approximate (r,z) coordinates corresponding to each of the data points $D_0$-$D_9$ are provided in Table 4 above.

Figure 11:
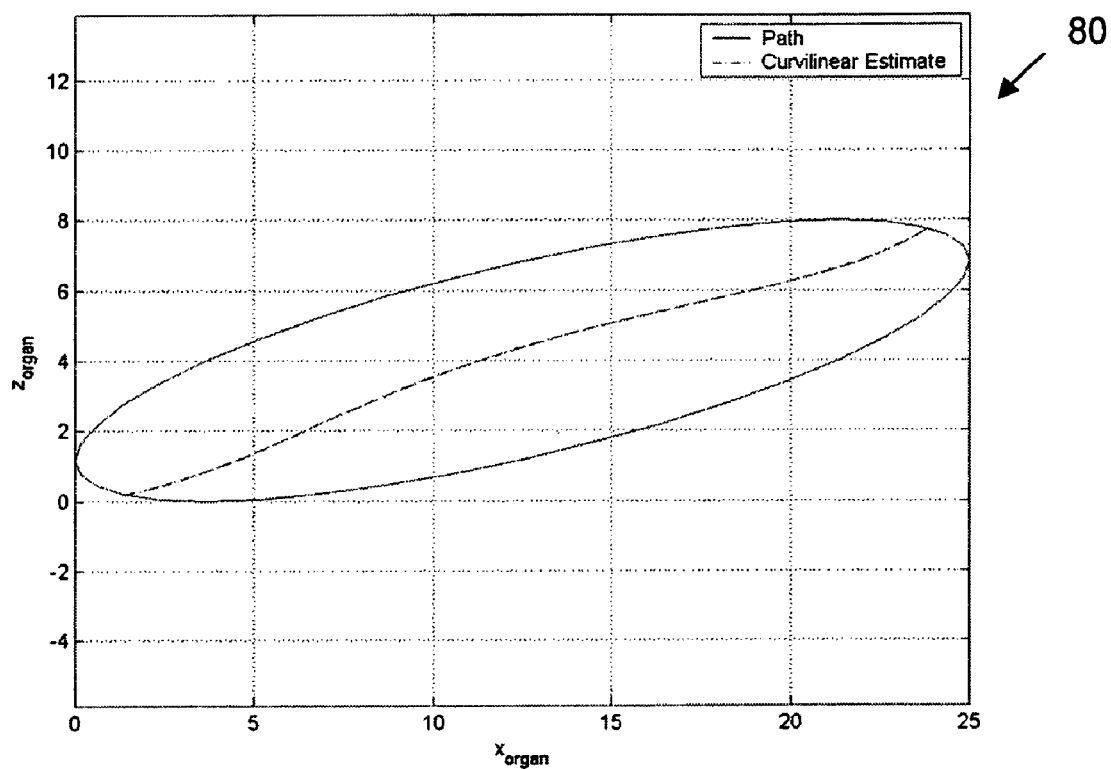
FIG. 11 is a graphical representation of an exemplary estimated path for a nonlinear correlation model in two dimensions.

FIG. 11 is a graphical representation 80 of an exemplary estimated path for a nonlinear correlation model. The graph 80 superimposes the nonlinear correlation model for the x and z directions on the path of movement, shown in FIG. 2, of the target 10. While the nonlinear correlation model is fairly accurate at about (x,z)=(2,0) and (x,z)=(23,8), the nonlinear correlation model has relatively large estimation errors for all of the other coordinates along the path of movement. Nevertheless, the nonlinear correlation model has an estimation error that may be smaller than the estimation error of the linear correlation model. The estimation errors are shown and described in more detail with reference to FIG. 20.

Figure 12:
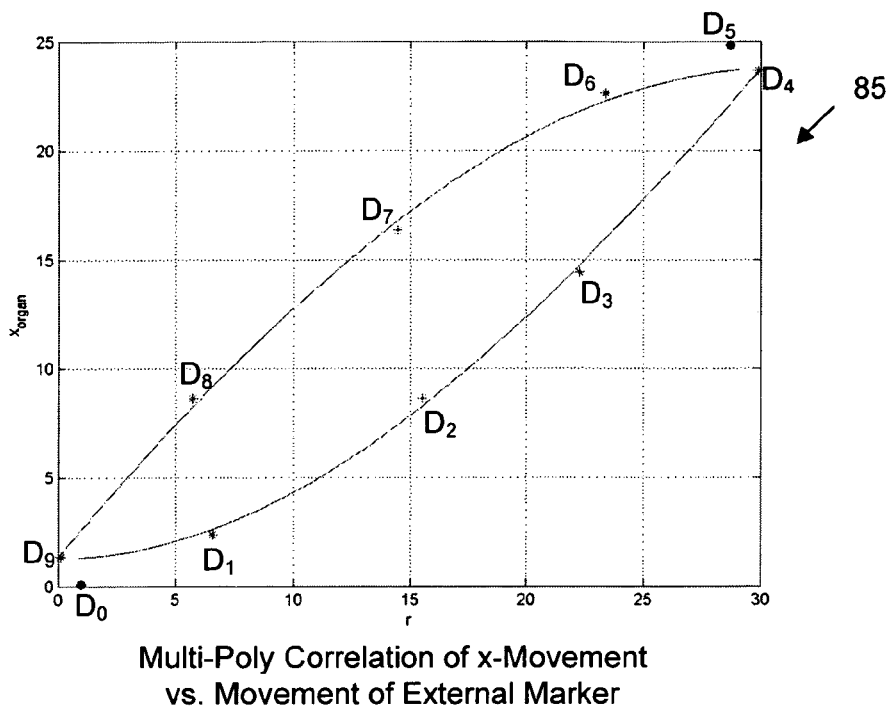
FIG. 12 is a graphical representation of an exemplary multi-poly correlation model of the path of movement in a first dimension, as a function of movement of an external marker.

FIG. 12 is a graphical representation 85 of an exemplary multi-poly correlation model of the path of movement in a first dimension, as a function of the displacement, r, of an external marker 10. In particular, the graph 85 shows the (r,x) coordinates from the data points $D_0$-$D_9$ above and superimposes a multi-poly correlation model (dashed line). The multi-poly correlation model also may be referred to herein as a curvilinear correlation model or, more generally, a nonlinear correlation model. The approximate (r,x) coordinates corresponding to each of the data points $D_0$-$D_9$ is provided in Table 3 above.

The multi-poly correlation model may be used to estimate the x displacement of the target 10 based on the speed, $\dot{r}$, and the direction of motion (i.e., the positive or negative sign of $\dot{r}$) of the external marker 25. In one embodiment, the directional indicators may be used to split the path of movement of the target 10 into two separate curvilinear paths. The directional indicators also may be used to distinguish the data points $D_1$-$D_4$ corresponding to the inspiration interval from the data points $D_6$-$D_9$ corresponding to the expiration interval. In another embodiment, this approach may be implemented with a third order polynomial, as described above, and the multi-poly correlation model may be described by the following equation:

$$x = \begin{cases} \sum_{n=0}^{3} a_n^+ r^n & \dot{r} \geq 0 \\ \sum_{n=0}^{3} a_n^- r^n & \dot{r} < 0 \end{cases}$$

In one embodiment, the foregoing equation essentially separates the data points into two separate groups according to their respective direction of motion of each data point. In particular, data points whose direction is positive (according to a predetermined sign convention) may be placed in a first data set and data points whose direction is negative may be placed in a second data set. The data sets may correspond to the inspiration and expiration intervals. However, in another embodiment, the data sets for each of the polynomial approximations may overlap. For example, data points that have a relatively small directional value may be placed in more than one data set, regardless of sign. As an example, the data points $D_0$, $D_4$, $D_5$, and $D_9$ may be placed in each of two data sets. Accordingly, the foregoing equations may be modified to account for these overlapping data sets. The outputs of multiple polynomials may be averaged for the data points that belong to more than one data set. In another embodiment, more than two polynomial approximations may be used to approximate the movement of the target 10.

Figure 13:
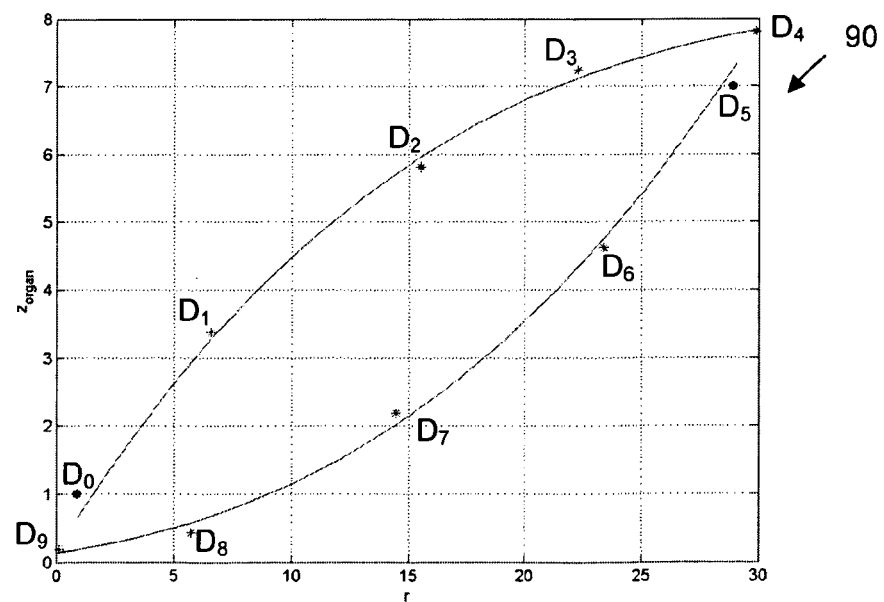
FIG. 13 is a graphical representation of an exemplary multi-poly correlation model of the path of movement in a second dimension, as a function of movement of an external marker.

FIG. 13 is a graphical representation 90 of an exemplary multi-poly correlation model of the path of movement in a second dimension, as a function of the displacement, r, of an external marker 10. In particular, the graph 90 shows the (r,z) coordinates from the data points $D_0$-$D_9$ above and superimposes a multi-poly correlation model (dashed line). The approximate (r,z) coordinates corresponding to each of the data points $D_0$-$D_9$ are provided in Table 4 above.

Figure 14:
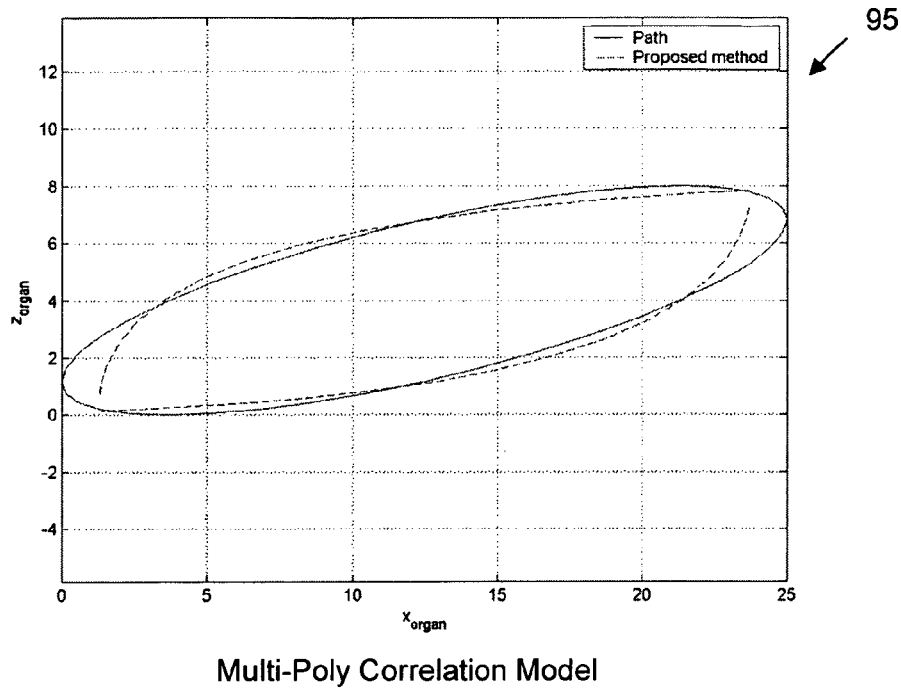
FIG. 14 is a graphical representation of an exemplary estimated path for a multi-poly correlation model in two dimensions.

FIG. 14 is a graphical representation 95 of an exemplary estimated path for a multi-poly correlation model. The graph 95 superimposes the multi-poly correlation model for the x and z directions on the path of movement, shown in FIG. 2, of the target 10. In comparison to the linear correlation model and third order nonlinear correlation model described above, the multi-poly correlation model is much more accurate for most, if not all, of the coordinates along the path of movement of the target 10.

The illustrated multi-poly correlation model includes two polynomial approximations. However, other embodiments may include more than two polynomial approximations. In another embodiment, the multi-poly correlation model also may include one or more linear approximations to approximate a portion of the path of movement.

Figure 15:
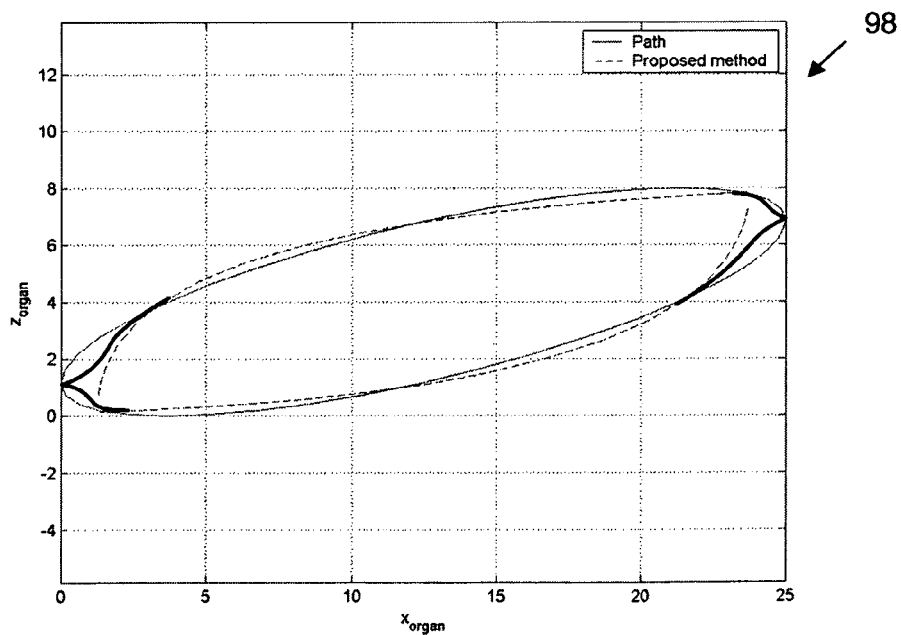
FIG. 15 is a graphical representation of exemplary polynomial matching approximations to link the individual polynomial approximations of the multi-poly correlation model of FIG. 14.

FIG. 15 is a graphical representation of exemplary polynomial matching approximations to link the individual polynomial approximations of the multi-poly correlation model of FIG. 14. In one embodiment, the matching approximations may link an inspiration polynomial approximation and an expiration polynomial approximation at about the region corresponding to the moments between the inspiration and expiration periods (near x=0 and x=25). Although two matching approximations are shown at each linking region (near x=0 and x=25), other embodiments may implement fewer or more matching approximations. In another embodiment, the matching approximations may include polynomial approximations, linear approximations, or a combination thereof.

Figure 16:
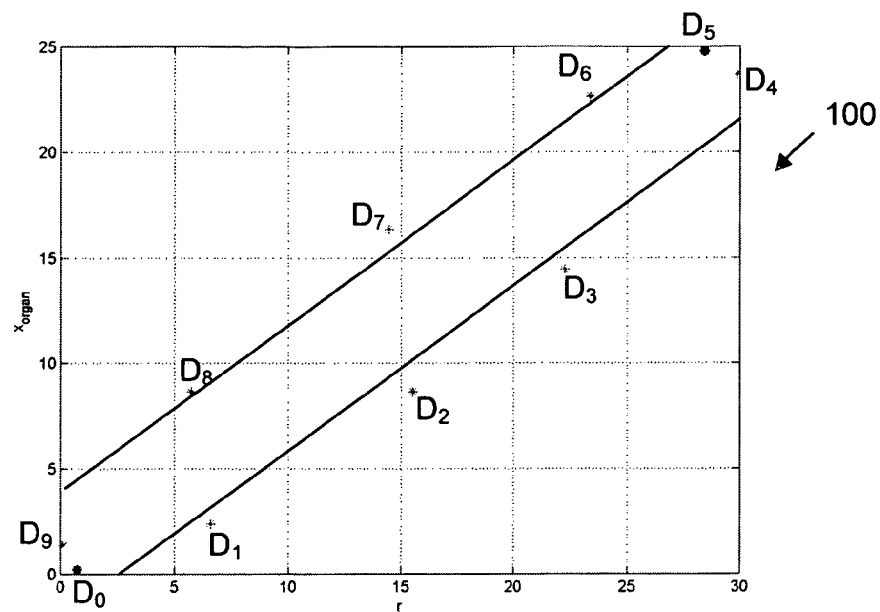
FIG. 16 is a graphical representation of an exemplary multi-linear correlation model of the path of movement in a first dimension, as a function of movement of an external marker.

FIG. 16 is a graphical representation 100 of an exemplary multi-linear correlation model of the path of movement in a first dimension, as a function of the displacement, r, of an external marker 10. The multi-linear correlation model also may be referred to herein, more generally, as a nonlinear correlation model. In particular, the graph 100 shows the (r,x) coordinates from the data points $D_0$-$D_9$ above and superimposes a multi-linear correlation model (dashed line). The approximate (r,x) coordinates corresponding to each of the data points $D_0$-$D_9$ is provided in Table 3 above.

The multi-linear correlation model may be used to estimate the x displacement of the target 10 based on the speed, $\dot{r}$, and the direction of motion (i.e., the positive or negative sign of $\dot{r}$) of the external marker 25, as described above. However, multiple linear approximations may be used instead of polynomial approximations. Linear or polynomial matching approximations also may be used to link the multiple linear approximations to one another, as described above.

Figure 17:
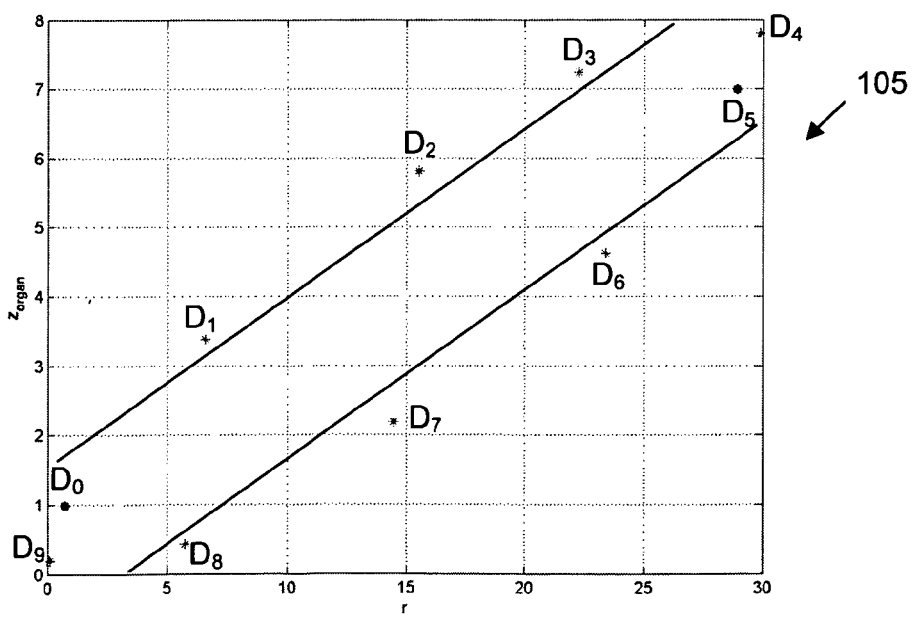
FIG. 17 is a graphical representation of an exemplary multi-linear correlation model of the path of movement in a second dimension, as a function of movement of an external marker.

FIG. 17 is a graphical representation 105 of an exemplary multi-linear correlation model of the path of movement in a second dimension, as a function of the displacement, r, of an external marker 10. In particular, the graph 105 shows the (r,z) coordinates from the data points $D_0$-$D_9$ above and superimposes a multi-linear correlation model (dashed line). The approximate (r,z) coordinates corresponding to each of the data points $D_0$-$D_9$ are provided in Table 4 above.

Figure 18:
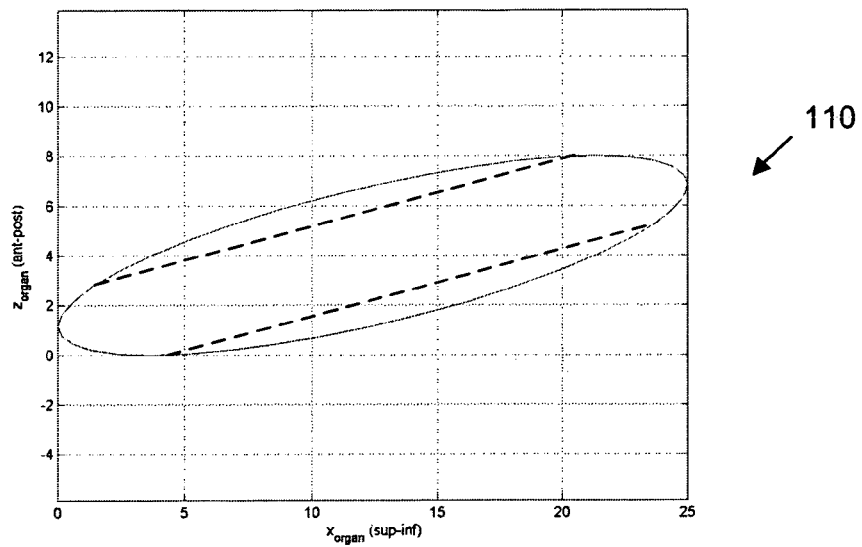
FIG. 18 is a graphical representation of an exemplary estimated path for a multi-linear correlation model in two dimensions.

FIG. 18 is a graphical representation 110 of an exemplary estimated path for a multi-linear correlation model. The graph 110 superimposes the multi-linear correlation model for the x and z directions on the path of movement, shown in FIG. 2, of the target 10. In comparison to the linear correlation model and third order nonlinear correlation model described above, the multi-linear correlation model is much more accurate for most, if not all, of the coordinates along the path of movement of the target 10. The multi-linear correlation model may or may not be more accurate than the multi-poly correlation model described above. In certain embodiments, the multi-linear correlation model includes two or more linear approximations. In another embodiment, the multi-linear correlation model also may include one or more polynomial approximations to approximate a portion of the path of movement.

Figure 19:
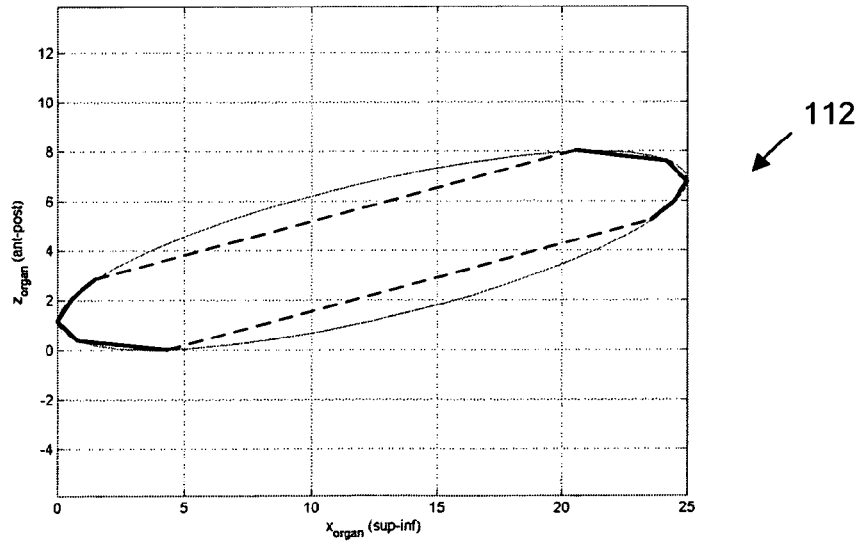
FIG. 19 is a graphical representation of exemplary linear matching approximations to link the individual linear approximations of the multi-linear correlation model of FIG. 18.

FIG. 19 is a graphical representation of exemplary linear matching approximations to link the individual linear approximations of the multi-linear correlation model of FIG. 18. In one embodiment, the matching approximations may link the two or more linear and/or polynomial approximations together. For example, the matching approximations may link an inspiration linear approximation and an expiration linear approximation at about the region corresponding to the moments between the inspiration and expiration periods (near x=0 and x=25). Although four matching approximations are shown at each linking region (near x=0 and x=25), other embodiments may implement fewer or more matching approximations. Furthermore, other embodiments may implement an odd number of matching approximations. In another embodiment, the matching approximations may include polynomial approximations, linear approximations, or a combination thereof.

Figure 20:
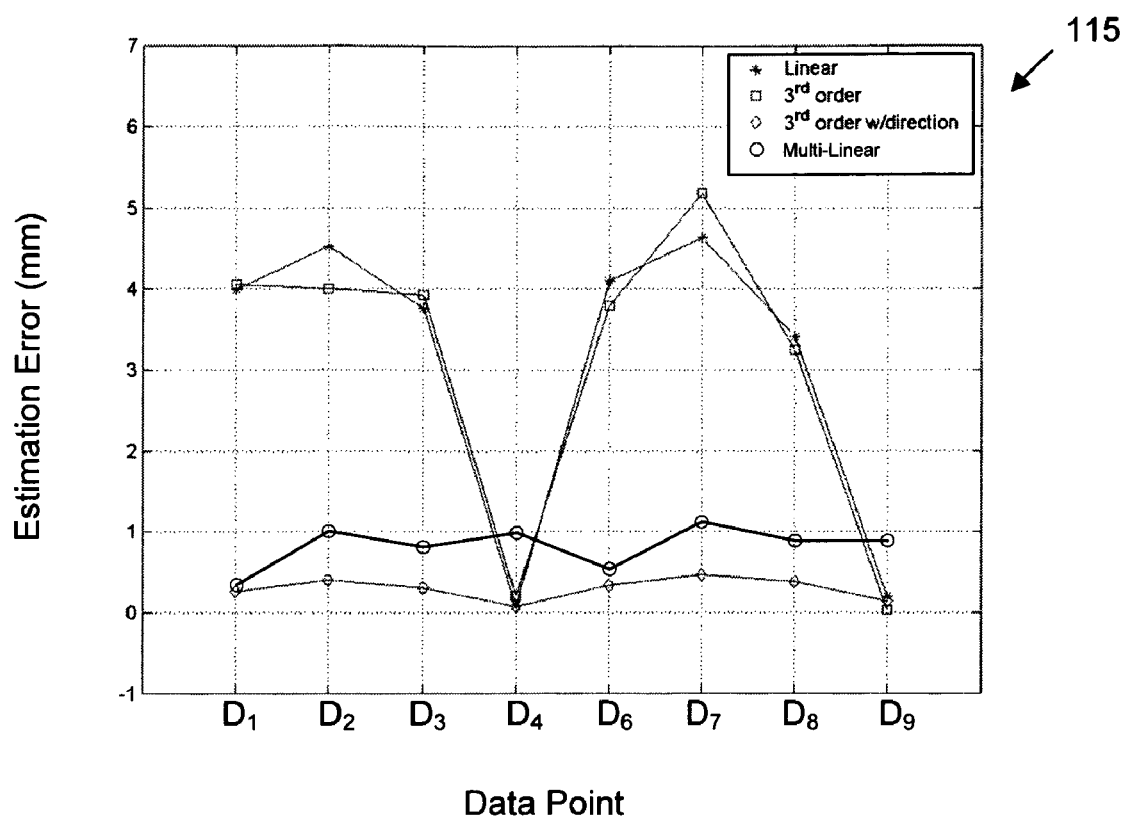
FIG. 20 is a graphical representation of exemplary estimation errors for a plurality of correlation models.

FIG. 20 is a graphical representation 115 of exemplary estimation errors for a plurality of correlation models. In particular, the graph 115 illustrates estimation errors for a linear correlation model (stars), a nonlinear polynomial correlation model (squares), a multi-poly correlation model (diamonds), and a multi-linear correlation model (circles) at data points $D_1$-$D_4$ and $D_6$-$D_9$ (data point $D_0$ might fall between data points $D_9$ and $D_0$; data point $D_5$ might fall between data points $D_4$ and $D_6$). The illustrated estimation errors for the nonlinear polynomial and multi-poly correlations models are specifically based on third order polynomial approximations, but may be based on higher order approximations in other embodiments.

The graph 115 shows that the polynomial correlation model has an estimation error that is slightly lower, for the most part, than the estimation error associated with the linear correlation model. However, the estimation error associated with the multi-linear and multi-poly correlation models are significantly lower than the estimation errors for the linear and nonlinear polynomial correlation models. In one embodiment, the estimation error for the multi-poly correlation model is less than one mm, compared to four or five mm for the linear and nonlinear polynomial correlation models. In another embodiment, the estimation error for the multi-poly correlation model may be approximately one-tenth of the estimation error for the linear and nonlinear polynomial correlation models. The estimation error for the multi-linear correlation model may be slighting higher than the estimation error for the multi-poly correlation model, but significantly lower compared to the estimation errors for the linear and nonlinear polynomial correlation models.

Figure 21:
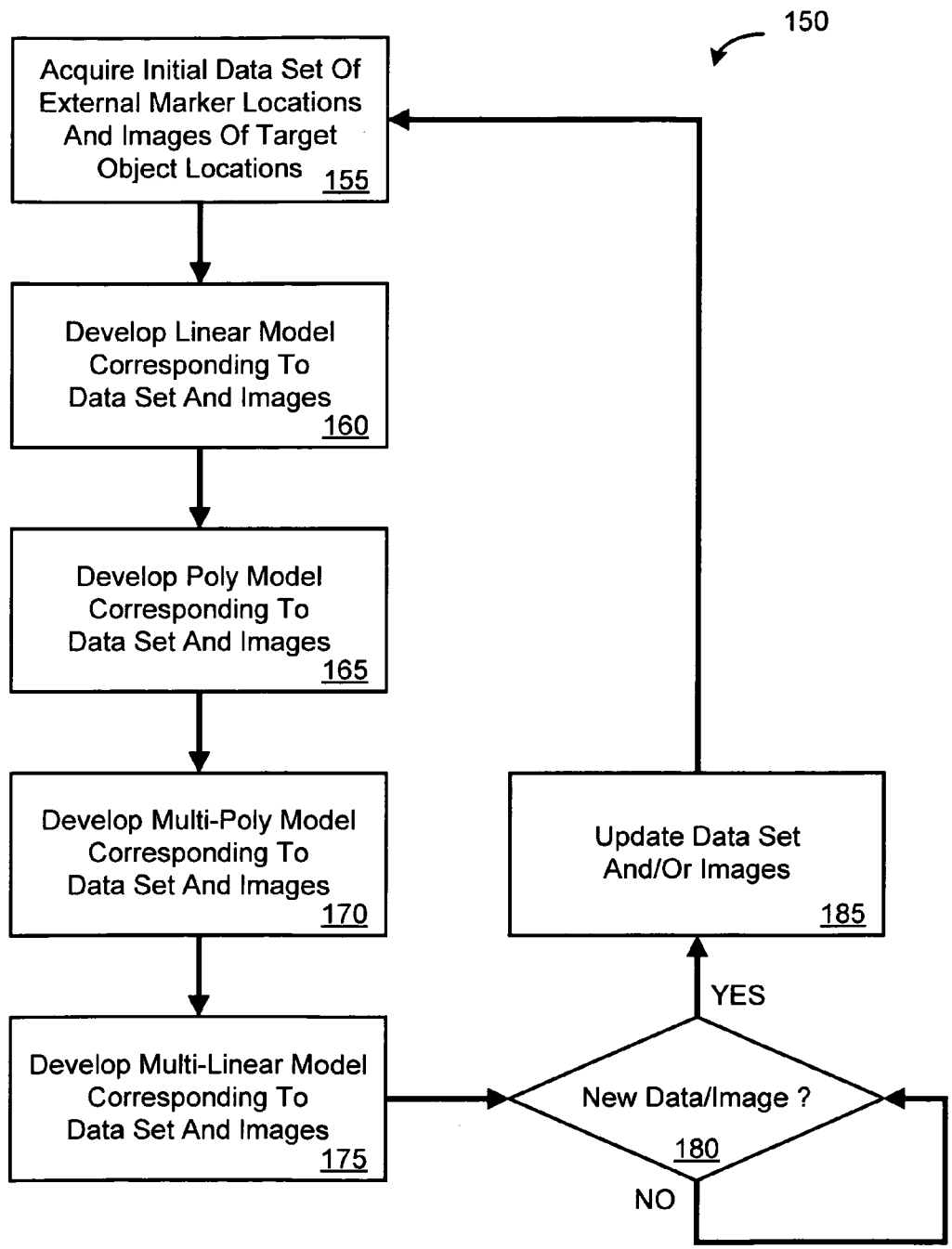
FIG. 21 illustrates one embodiment of a modeling method.

FIG. 21 illustrates one embodiment of a modeling method 150. In one embodiment, the depicted modeling method 150 may be implemented in hardware, software, and/or firmware on a treatment planning system, such as the treatment planning system 530 of FIG. 24. Although the modeling method 150 is described in terms of the treatment planning system 530, embodiments the modeling method 150 may be implemented on another system or independent of the treatment planning system 530.

The illustrated modeling method 150 begins and the treatment planning system 530 acquires 155 an initial data set of locations of an external marker 25. The treatment planning system 530 also acquires 155 one or more images of the target 10. The location of the target 10 may be derived from these images. The position of the target 10 also may be determined relative to the location of the external marker 25.

The treatment planning system 530 subsequently uses the data set and images to develop 160 a linear correlation model, as described above with reference to FIGS. 7-9. The treatment planning system 530 also uses the data set and images to develop 165 a nonlinear polynomial correlation model, as described above with reference to FIG. 9-11. The treatment planning system 530 also uses the data set and images to develop 170 a multi-poly correlation model, as described above with reference to FIG. 12-14. The treatment planning system 530 also uses the data set and images to develop 175 a multi-linear correlation model, as described above with reference to FIG. 16-18. Although the illustrated modeling method 150 develops several types of correlation models, other embodiments of the modeling method 150 may develop fewer or more correlation models, including some or all of the correlation models described herein.

The treatment planning system 530 maintains these correlation models and, in certain embodiments, monitors 180 for or acquires new data and/or images. When new data or images are received, the treatment planning system updates 185 the data set and or the images and may iteratively develop new models based on the new information. In this way, the modeling method 150 may maintain the correlation models in real-time.

Figure 22:
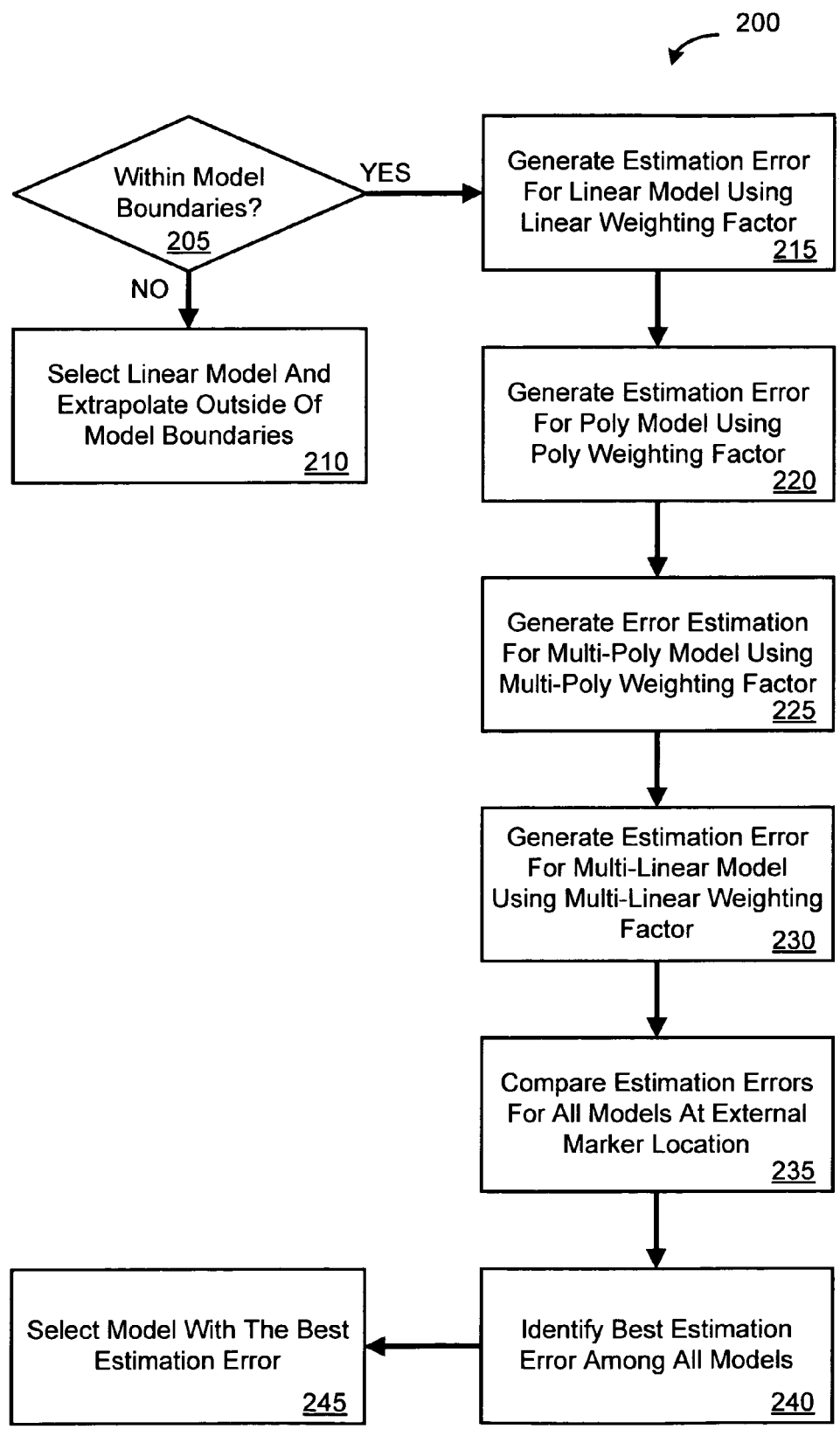
FIG. 22 illustrates one embodiment of a selection method.

FIG. 22 illustrates one embodiment of a selection method 200. In one embodiment, the depicted selection method 200 may be implemented in hardware, software, and/or firmware on a treatment planning system, such as the treatment planning system 530 of FIG. 24. Although the selection method 200 is described in terms of the treatment planning system 530, embodiments the selection method 200 may be implemented on another system or independent of the treatment planning system 530.

The illustrated selection method 200 begins and the treatment planning system 530 determines 205 if the displacement of the external marker 25 is within the boundaries of the various correlation models. For example, many of the correlation models described above have a displacement range between approximately zero and 30 mm. A patient may potentially inhale or exhale in a way that moves the external marker 25 outside of a correlation model range. If the displacement of the external marker 25 is not within the range of the correlation models, then the treatment planning system 530 may select 210 the linear correlation model and extrapolate outside of the model boundaries. Alternatively, the treatment planning system 530 may select another correlation model such as the multi-linear correlation model and determine an estimated location of the target 10 from the selected correlation model.

If the displacement of the external marker 25 is within the range of the correlation models, then the treatment planning system 530 may generate 215 an estimation error for the linear correlation model. In generating 215 the estimation error, the treatment planning system 530 may use a predetermined linear weighting factor that increases or decreases the estimation error. In this way, the treatment planning system 530 may give priority to certain types of correlation models based on a user selection, a type of treatment, or another treatment planning or delivery factor. In another embodiment, the treatment planning system 530 may have previously calculated an estimation error for the linear correlation model.

The treatment planning system 530 also generates 220 an estimation error for the nonlinear polynomial model. The treatment planning system 530 may use a predetermined polynomial weighting factor in generating 220 the estimation error. The treatment planning system 530 also generates 225 an estimation error for the multi-poly model. The treatment planning system 530 may use a predetermined multi-poly weighting factor in generating 225 the estimation error. The treatment planning system 530 also generates 230 an estimation error for the multi-linear model. The treatment planning system 530 may use a predetermined multi-linear weighting factor in generating 230 the estimation error. In another embodiment, one or more of the estimation errors may be generated previously.

The treatment planning system 530 subsequently compares 235 all of the estimation errors 235 for all of the correlation models. Alternatively, the treatment planning system 530 may compare some, but not all of the of the estimation errors. In one embodiment, the treatment planning system 530 compares the estimation errors only at the current or location of the external marker 25. In another embodiment, the treatment planning system 530 may generate a composite estimation error based on two or more marker locations for each of the correlation models.

The treatment planning system 530 then identifies 240 the best estimation error according to any rules, weighting factors, or other predetermined considerations, and selects 245 the identified correlation model for use. In one embodiment, the treatment planning system 530 may implement the modeling method 150 and/or the selection method 200 each time a new data point or image is received. In another embodiment, the treatment planning system 530 may implement the modeling method 150 and/or the selection method 200 less frequently or independently of one another. For example, the treatment planning system 530 may develop new correlation models once for every respiratory period and evaluate model selection multiple times during each respiratory period. In certain embodiments, the treatment planning system 530 may use linear or polynomial matching approximations to switch from one correlation model to another. In this way, the correlation models may be blended and the transition from one correlation model to another may be smooth and imperceptible to a patient.

Figure 23:
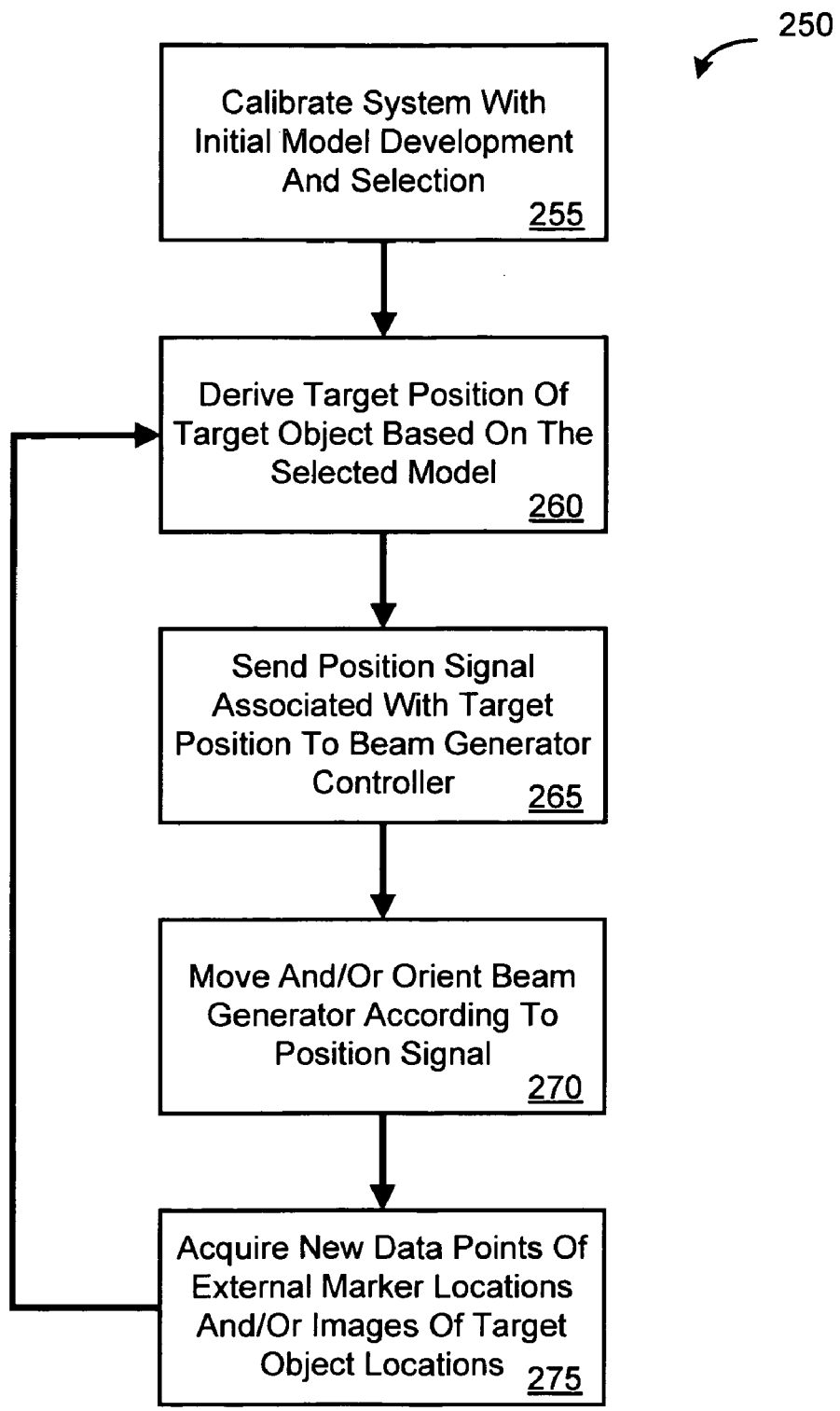
FIG. 23 illustrates one embodiment of a tracking method.

FIG. 23 illustrates one embodiment of a tracking method 250. In one embodiment, the tracking method 250 may be implemented in conjunction with a treatment system such as the treatment system 500 of FIG. 24. Furthermore, the depicted tracking method 250 may be implemented in hardware, software, and/or firmware on a treatment system 500. Although the tracking method 250 is described in terms of the treatment system 500, embodiments the tracking method 250 may be implemented on another system or independent of the treatment system 500.

The illustrated tracking method 250 begins and the treatment system 500 performs calibration 255 to initialize model development and selection. In one embodiment, such calibration includes performing the modeling method 150 and the selection method 200 prior to treatment delivery. In another embodiment, the modeling method 150 and/or the selection method 200 may be performed multiple times to establish historical data.

After the tracking system 500 is calibrated, the tracking system 500 derives 260 a target position of the target 10 based on the selected correlation model. As described above, the target location of the target 10 may be related to the known position of the external marker 25 and derived from one of the correlation models. The tracking system 265 subsequently sends 265 a position signal indicating the target position to a beam generator controller. In one embodiment, the treatment system 500 delivers the position signal to a treatment delivery system such as the treatment delivery system 550 of FIG. 24. The treatment delivery system 550 then moves 270 and orients the beam generator such as the radiation source 552 of FIG. 24. The treatment delivery system 550 and radiation source 552 are described in more detail below.

The treatment planning system 530 continues to acquire 275 new data points of the external marker 25 and new images of the target 10. In one embodiment, the treatment planning system 530 may repeatedly develop models according to the modeling method 150 and select a model according to the selection method 200, as described above. In another embodiment, the treatment planning system 530 may select and use one model to derive multiple target positions. The tracking method 250 may continue in this manner of developing one or more models, selecting a model, and delivering treatment according to the selected model for the duration of a treatment session.

Figure 24:
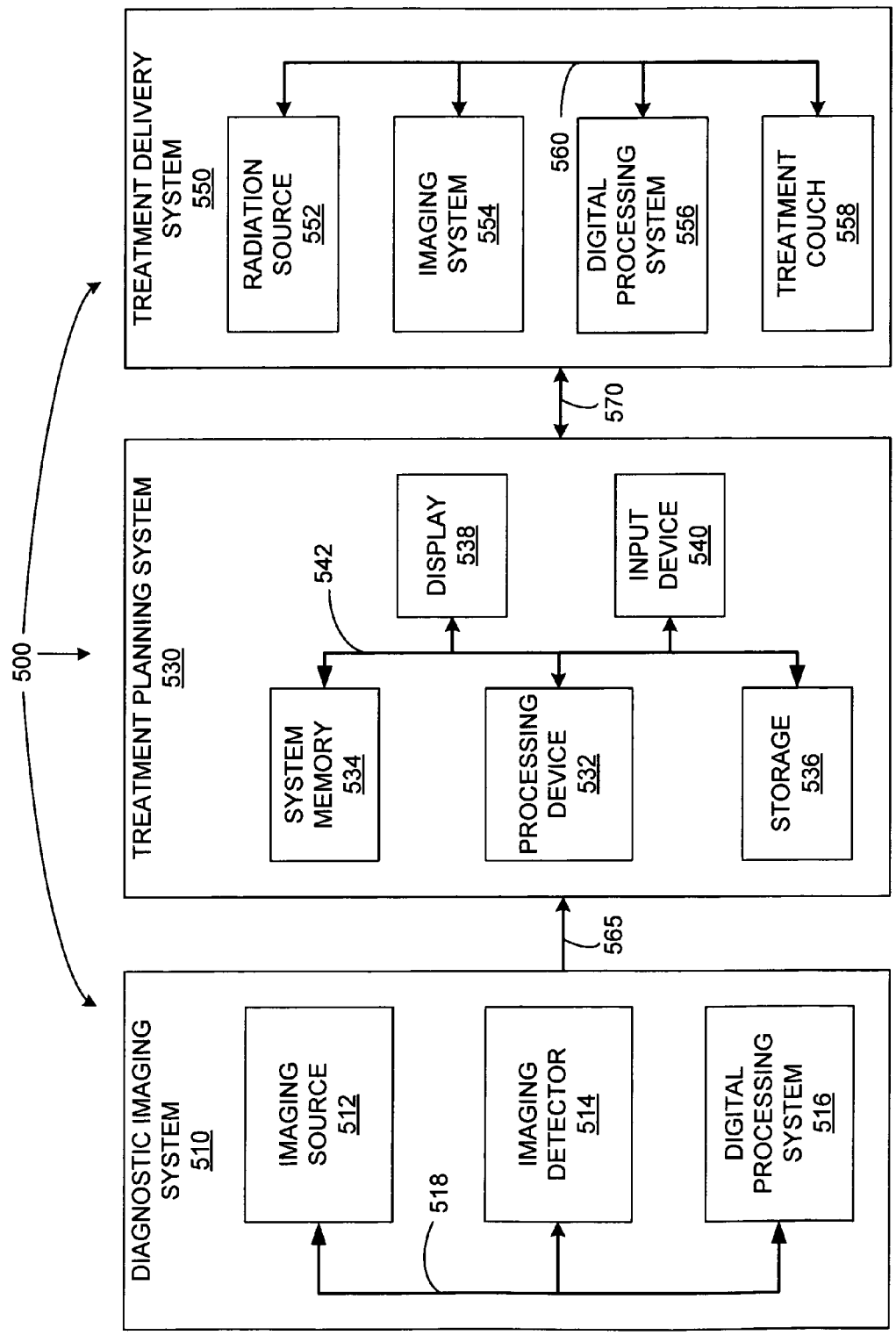
FIG. 24 illustrates one embodiment of a treatment system that may be used to perform radiation treatment in which embodiments of the present invention may be implemented.

FIG. 24 illustrates one embodiment of a treatment system 500 that may be used to perform radiation treatment in which features of the present invention may be implemented. The depicted treatment system 500 includes a diagnostic imaging system 510, a treatment planning system 530, and a treatment delivery system 550. In other embodiments, the treatment system 500 may include fewer or more component systems.

The diagnostic imaging system 510 is representative of any system capable of producing medical diagnostic images of a volume of interest (VOI) in a patient, which images may be used for subsequent medical diagnosis, treatment planning, and/or treatment delivery. For example, the diagnostic imaging system 510 may be a computed tomography (CT) system, a magnetic resonance imaging (MRI) system, a positron emission tomography (PET) system, an ultrasound system, or another similar imaging system. For ease of discussion, any specific references herein to a particular imaging system such as a CT x-ray imaging system is representative of the diagnostic imaging system 510, generally, and does not preclude other imaging modalities, unless noted otherwise.

The illustrated diagnostic imaging system 510 includes an imaging source 512, an imaging detector 514, and a digital processing system 516. The imaging source 512, imaging detector 514, and digital processing system 516 are coupled to one another via a communication channel 518 such as a bus. In one embodiment, the imaging source 512 generates an imaging beam (e.g., x-rays, ultrasonic waves, radio frequency waves, etc.) and the imaging detector 514 detects and receives the imaging beam. Alternatively, the imaging detector 514 may detect and receive a secondary imaging beam or an emission stimulated by the imaging beam from the imaging source (e.g., in an MRI or PET scan). In one embodiment, the diagnostic imaging system 510 may include two or more diagnostic imaging sources 512 and two or more corresponding imaging detectors 514. For example, two x-ray sources 512 may be disposed around a patient to be imaged, fixed at an angular separation from each other (e.g., 90 degrees, 45 degrees, etc.) and aimed through the patient toward corresponding imaging detectors 514, which may be diametrically opposed to the imaging sources 514. A single large imaging detector 514, or multiple imaging detectors 514, also may be illuminated by each x-ray imaging source 514. Alternatively, other numbers and configurations of imaging sources 512 and imaging detectors 514 may be used.

The imaging source 512 and the imaging detector 514 are coupled to the digital processing system 516 to control the imaging operations and process image data within the diagnostic imaging system 510. In one embodiment, the digital processing system 516 may communicate with the imaging source 512 and the imaging detector 514. Embodiments of the digital processing system 516 may include one or more general-purpose processors (e.g., a microprocessor), special purpose processors such as a digital signal processor (DSP), or other type of devices such as a controller or field programmable gate array (FPGA). The digital processing system 516 also may include other components (not shown) such as memory, storage devices, network adapters, and the like. In one embodiment, the digital processing system 516 generates digital diagnostic images in a standard format such as the Digital Imaging and Communications in Medicine (DICOM) format. In other embodiments, the digital processing system 516 may generate other standard or non-standard digital image formats.

Additionally, the digital processing system 516 may transmit diagnostic image files such as DICOM files to the treatment planning system 530 over a data link 560. In one embodiment, the data link 560 may be a direct link, a local area network (LAN) link, a wide area network (WAN) link such as the Internet, or another type of data link. Furthermore, the information transferred between the diagnostic imaging system 510 and the treatment planning system 530 may be either pulled or pushed across the data link 560, such as in a remote diagnosis or treatment planning configuration. For example, a user may utilize embodiments of the present invention to remotely diagnose or plan treatments despite the existence of a physical separation between the system user and the patient.

The illustrated treatment planning system 530 includes a processing device 532, a system memory device 534, an electronic data storage device 536, a display device 538, and an input device 540. The processing device 532, system memory 534, storage 536, display 538, and input device 540 may be coupled together by one or more communication channel 542 such as a bus.

The processing device 532 receives and processes image data. The processing device 532 also processes instructions and operations within the treatment planning system 530. In certain embodiments, the processing device 532 may include one or more general-purpose processors (e.g., a microprocessor), special purpose processors such as a digital signal processor (DSP), or other types of devices such as a controller or field programmable gate array (FPGA).

In particular, the processing device 532 may be configured to execute instructions for performing treatment operations discussed herein. For example, the processing device 532 may identify a non-linear path of movement of a target within a patient and develop a non-linear model of the non-linear path of movement. In another embodiment, the processing device 532 may develop the non-linear model based on a plurality of position points and a plurality of direction indicators. In another embodiment, the processing device 532 may generate a plurality of correlation models and select one of the plurality of models to derive a position of the target. Furthermore, the processing device 532 may facilitate other diagnosis, planning, and treatment operations related to the operations described herein.

In one embodiment, the system memory 534 may include random access memory (RAM) or other dynamic storage devices. As described above, the system memory 534 may be coupled to the processing device 532 by the communication channel 542. In one embodiment, the system memory 534 stores information and instructions to be executed by the processing device 532. The system memory 534 also may be used for storing temporary variables or other intermediate information during execution of instructions by the processing device 532. In another embodiment, the system memory 534 also may include a read only memory (ROM) or other static storage device for storing static information and instructions for the processing device 532.

In one embodiment, the storage 536 is representative of one or more mass storage devices (e.g., a magnetic disk drive, tape drive, optical disk drive, etc.) to store information and instructions. The storage 536 and/or the system memory 534 also may be referred to as machine readable media. In a specific embodiment, the storage 536 may store instructions to perform the modeling operations discussed herein. For example, the storage 536 may store instructions to acquire and store data points, acquire and store images, identify non-linear paths, develop linear and/or non-linear correlation models, select a correlation model from a plurality of models, and so forth. In another embodiment, the storage 536 may include one or more databases.

In one embodiment, the display 538 may be a cathode ray tube (CRT) display, a liquid crystal display (LCD), or another type of display device. The display 538 displays information (e.g., a two-dimensional or three-dimensional representation of the VOI) to a user. The input device 540 may include one or more user interface devices such as a keyboard, mouse, trackball, or similar device. The input device(s) 540 may also be used to communicate directional information, to select commands for the processing device 532, to control cursor movements on the display 538, and so forth.

Although one embodiment of the treatment planning system 530 is described herein, the described treatment planning system 530 is only representative of an exemplary treatment planning system 530. Other embodiments of the treatment planning system 530 may have many different configurations and architectures and may include fewer or more components. For example, other embodiments may include multiple buses, such as a peripheral bus or a dedicated cache bus. Furthermore, the treatment planning system 530 also may include Medical Image Review and Import Tool (MIRIT) to support DICOM import so that images can be fused and targets delineated on different systems and then imported into the treatment planning system 530 for planning and dose calculations. In another embodiment, the treatment planning system 530 also may include expanded image fusion capabilities that allow a user to plan treatments and view dose distributions on any one of various imaging modalities such as MRI, CT, PET, and so forth. Furthermore, the treatment planning system 530 may include one or more features of convention treatment planning systems.

In one embodiment, the treatment planning system 530 may share a database on the storage 536 with the treatment delivery system 550 so that the treatment delivery system 550 may access the database prior to or during treatment delivery. The treatment planning system 530 may be linked to treatment delivery system 550 via a data link 570, which may be a direct link, a LAN link, or a WAN link, as discussed above with respect to data link 560. Where LAN, WAN, or other distributed connections are implemented, any of components of the treatment system 500 may be in decentralized locations so that the individual systems 510, 530, 550 may be physically remote from one other. Alternatively, some or all of the functional features of the diagnostic imaging system 510, the treatment planning system 530, or the treatment delivery system 550 may be integrated with each other within the treatment system 500.

The illustrated treatment delivery system 550 includes a radiation source 552, an imaging system 554, a digital processing system 556, and a treatment couch 558. The radiation source 552, imaging system 554, digital processing system 556, and treatment couch 558 may be coupled to one another via one or more communication channel 560. One example of a treatment delivery system 550 is shown and described in more detail with reference to FIG. 25.

In one embodiment, the radiation source 552 is a therapeutic or surgical radiation source 552 to administer a prescribed radiation dose to a target volume in conformance with a treatment plan. For example, the target volume may be an internal organ, a tumor, a region. For convenience, reference herein to the target volume or a target refers to any whole or partial organ, tumor, region, or other delineated volume that is the subject of a treatment plan.

In one embodiment, the imaging system 554 of the treatment delivery system 550 captures intra-treatment images of a patient volume, including the target volume, for registration or correlation with the diagnostic images described above in order to position the patient with respect to the radiation source. Similar to the diagnostic imaging system 510, the imaging system 554 of the treatment delivery system 550 may include one or more sources and one or more detectors.

The treatment delivery system 550 also may include a digital processing system 556 to control the radiation source 552, the imaging system 554, and a treatment couch 558, which is representative of any patient support device. The digital processing system 556 may include one or more general-purpose processors (e.g., a microprocessor), special purpose processors such as a digital signal processor (DSP), or other devices such as a controller or field programmable gate array (FPGA). Additionally, the digital processing system 556 may include other components (not shown) such as memory, storage devices, network adapters, and the like.

Figure 25:
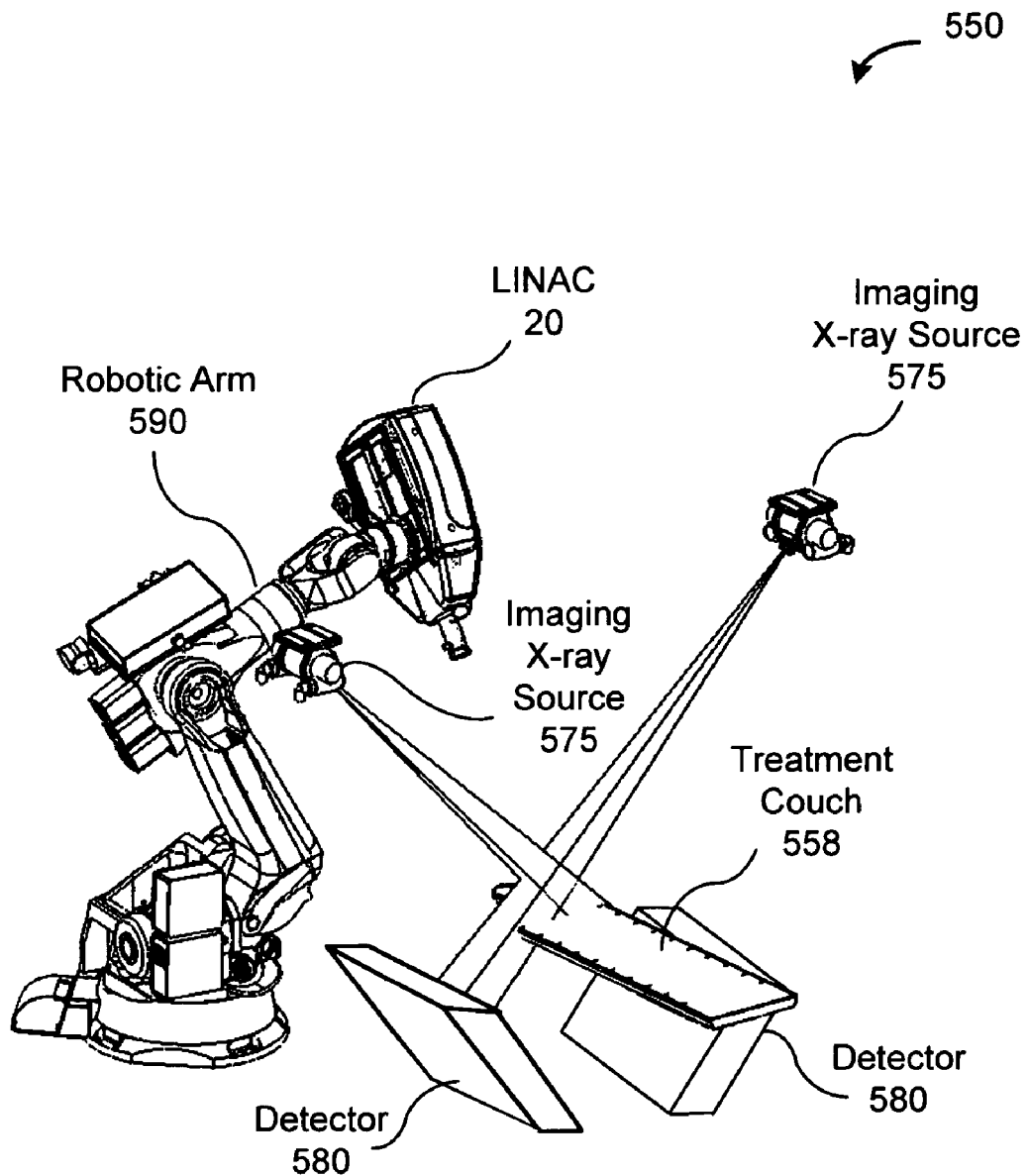
FIG. 25 is a schematic block diagram illustrating one embodiment of a treatment delivery system.

FIG. 25 is a schematic block diagram illustrating one embodiment of a treatment delivery system 550. The depicted treatment delivery system 550 includes a radiation source 552, in the form of a linear accelerator (LINAC) 20, and a treatment couch 558, as described above. The treatment delivery system 550 also includes multiple imaging x-ray sources 575 and detectors 580. The two x-ray sources 575 may be nominally aligned to project imaging x-ray beams through a patient from at least two different angular positions (e.g., separated by 90 degrees, 45 degrees, etc.) and aimed through the patient on the treatment couch 558 toward the corresponding detectors 580. In another embodiment, a single large imager may be used to be illuminated by each x-ray imaging source 575. Alternatively, other quantities and configurations of imaging sources 575 and detectors 580 may be used. In one embodiment, the treatment delivery system 550 may be an image-guided, robotic-based radiation treatment system (e.g., for performing radiosurgery) such as the CYBERKNIFE® system developed by Accuray Incorporated of California.

In the illustrated embodiment, the LINAC 20 is mounted on a robotic arm 590. The robotic arm 590 may have multiple (e.g., 5 or more) degrees of freedom in order to properly position the LINAC 20 to irradiate a target such as a pathological anatomy with a beam delivered from many angles in an operating volume around the patient. The treatment implemented with the treatment delivery system 550 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (mono-fraction) or in a small number of sessions (hypo-fractionation) as determined during treatment planning. In one embodiment, the treatment delivery system 550 delivers radiation beams according to the treatment plan without fixing the patient to a rigid, external frame to register the intra-operative position of the target volume with the position of the target volume during the pre-operative treatment planning phase.

As described above, the digital processing system 556 may implement algorithms to register images obtained from the imaging system 554 with pre-operative treatment planning images obtained from the diagnostic imaging system 510 in order to align the patient on the treatment couch 558 within the treatment delivery system 550. Additionally, these images may be used to precisely position the radiation source 552 with respect to the target volume or target.

In one embodiment, the treatment couch 558 may be coupled to second robotic arm (not shown) having multiple degrees of freedom. For example, the second arm may have five rotational degrees of freedom and one substantially vertical, linear degree of freedom. Alternatively, the second arm may have six rotational degrees of freedom and one substantially vertical, linear degree of freedom. In another embodiment, the second arm may have at least four rotational degrees of freedom. Additionally, the second arm may be vertically mounted to a column or wall, or horizontally mounted to pedestal, floor, or ceiling. Alternatively, the treatment couch 558 may be a component of another mechanism, such as the AXUM® treatment couch developed by Accuray Incorporated of California. In another embodiment, the treatment couch 558 may be another type of treatment table, including a conventional treatment table.

Although one exemplary treatment delivery system 550 is described above, the treatment delivery system 550 may be another type of treatment delivery system. For example, the treatment delivery system 550 may be a gantry based (isocentric) intensity modulated radiotherapy (IMRT) system, in which a radiation source 552 (e.g., a LINAC 20) is mounted on the gantry in such a way that it rotates in a plane corresponding to an axial slice of the patient. Radiation may be delivered from several positions on the circular plane of rotation. In another embodiment, the treatment delivery system 550 may be a stereotactic frame system such as the GAM-MAKNIFE®, available from Elekta of Sweden.

Figure 26:
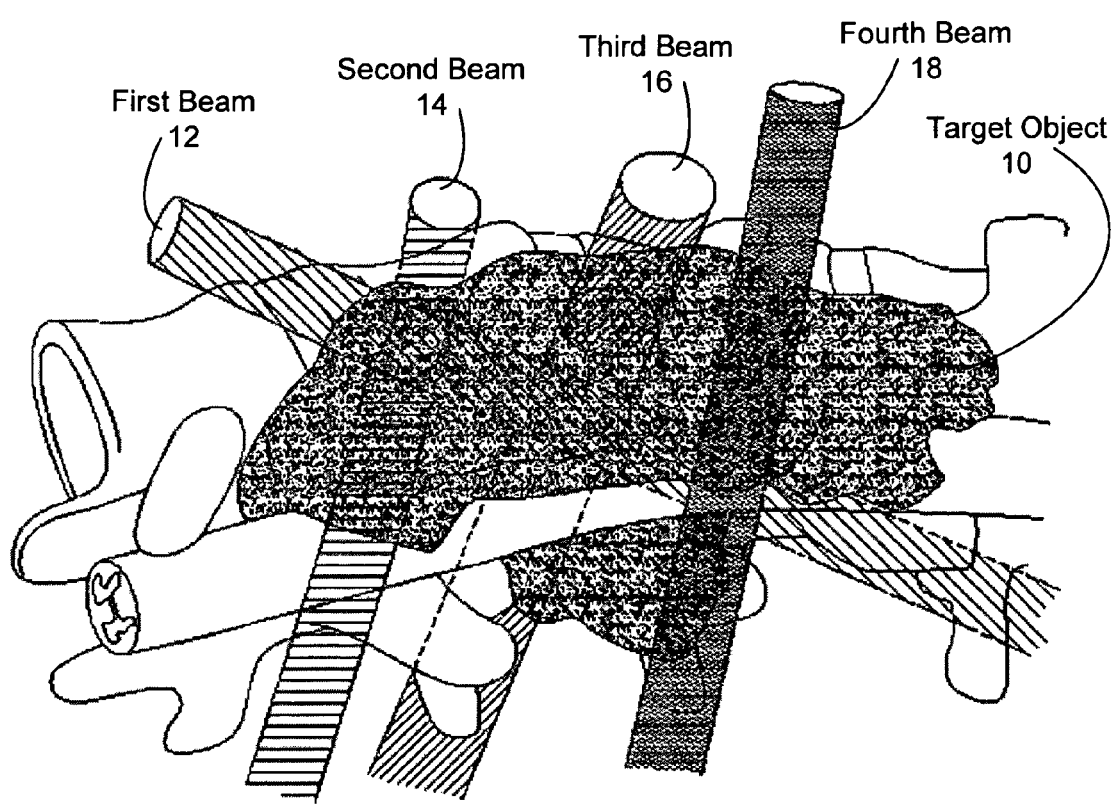
FIG. 26 illustrates a three-dimensional perspective view of a radiation treatment process.

FIG. 26 illustrates a three-dimensional perspective view of a radiation treatment process. In particular, FIG. 26 depicts several radiation beams directed at a target 10. In one embodiment, the target 10 may be representative of an internal organ, a region within a patient, a pathological anatomy such as a tumor or lesion, or another type of object or area of a patient. The target 10 also may be referred to herein as a target region, a target volume, and so forth, but each of these references is understood to refer generally to the target 10, unless indicated otherwise.

The illustrated radiation treatment process includes a first radiation beam 12, a second radiation beam 14, a third radiation beam 16, and a fourth radiation beam 18. Although four radiation beams 12-18 are shown, other embodiments may include fewer or more radiation beams. For convenience, reference to one radiation beam 12 is representative of all of the radiation beams 12-18, unless indicated otherwise. Additionally, the treatment sequence for application of the radiation beams 12-18 may be independent of their respective ordinal designations.

In one embodiment, the four radiation beams 12 are representative of beam delivery based on conformal planning, in which the radiation beams 12 pass through or terminate at various points within target region 10. In conformal planning, some radiation beams 12 may or may not intersect or converge at a common point in three-dimensional space. In other words, the radiation beams 12 may be non-isocentric in that they do not necessarily converge on a single point, or isocenter. However, the radiation beams 12 may wholly or partially intersect at the target 10 with one or more other radiation beams 12.

In another embodiment, the intensity of each radiation beam 12 may be determined by a beam weight that may be set by an operator or by treatment planning software. The individual beam weights may depend, at least in part, on the total prescribed radiation dose to be delivered to target 10, as well as the cumulative radiation dose delivered by some or all of the radiation beams 12. For example, if a total prescribed dose of 3500 cGy is set for the target 10, the treatment planning software may automatically predetermine the beam weights for each radiation beam 12 in order to balance conformality and homogeneity to achieve that prescribed dose. Conformality is the degree to which the radiation dose matches (conforms to) the shape and extent of the target 10 (e.g., tumor) in order to avoid damage to critical adjacent structures. Homogeneity is the uniformity of the radiation dose over the volume of the target 10. The homogeneity may be characterized by a dose volume histogram (DVH), which ideally may be a rectangular function in which 100 percent of the prescribed dose would be over the volume of the target 10 and would be zero everywhere else.

The method described above offers many advantages, compared to currently know methods that are restricted to linear models. A first advantage, of course, is that this method does not assume linear movement, and applies to any general movement for internal organs. This method therefore realistically takes account of the actual motion of the internal organs. A second advantage is that this method can successfully identify the correlation model for organs that traverse along different paths during inspiration and expiration, respectively.

In sum, a method and system are presented for identifying curvilinear internal organ movements. The above described method and system can detect and identify whether a patient's internal organ moves (during respiration of the patient) along different paths during the inspiration and the expiration phases of the respiration, respectively. The above-described method allows a correlation model to be constructed that can accurately estimate the position of an internal organ that either undergoes curvilinear movement, or moves along different paths during the inspiration and the expiration phases of the respiration, or both. Any other types of non-linear motion of an organ can also be fitted using curvilinear models as described above, by choosing appropriate parameter fitting models, e.g. higher-order polynomial fitting methods, as just one example. The method described above permits the targeting of internal lesions and/or tumors that move with respiration (or other patient motion), for purpose of delivering therapeutic radiation to the lesions and tumors.

While the method and system above have been described in conjunction with respiratory motion of the patient, other embodiments may track asymmetric, curvilinear (or otherwise nonlinear) motion of the internal organs that occur during any other type of motion of the patient, e.g. heartbeat.

While the correlation method and system have been particularly shown and described with reference to specific embodiments, it should be understood by those skilled in the art that various changes in form and detail may be made therein without departing from the spirit and scope of the invention.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by treatment planning software, such as the application of a beam (e.g., radiation, acoustic, etc.).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A computer-implemented method, comprising:
   receiving a plurality of data points representative of a corresponding plurality of positions over time of an external marker associated with respiration of a patient;
   receiving a plurality of images of an internal target of the patient, the plurality of images corresponding in time to the plurality of data points;
   developing, using a processing device, a non-linear correlation model of a non-linear path of movement of the target based on the plurality of data points and the plurality of images to correlate a plurality of positions of the internal target with the plurality of positions of the external marker, wherein developing the non-linear correlation model comprises:
   generating an inspiration approximation associated with the non-linear path of movement of the target over an inspiration interval of the non-linear path;
   generating an expiration approximation associated with the non-linear path of movement of the target over an expiration interval of the non-linear path; and generating one or more matching approximations to link the inspiration approximation and the expiration approximation.

2. The method of claim 1, wherein the non-linear correlation model comprises a polynomial approximation of the non-linear path of movement of the target.

3. The method of claim 1, wherein the non-linear correlation model comprises a multi-linear model having a plurality of linear approximations connected at a non-zero angle.

4. The method of claim 1, wherein developing the non-linear correlation model comprises generating one or derivatives from the plurality of data points, the one or more derivatives comprising one or more directional indicators.

5. The method of claim 1, wherein the inspiration approximation and the expiration approximation are derived from at least partially overlapping data sets.

6. The method of claim 1, further comprising deriving a target position of the target based on the non-linear correlation model.

7. The method of claim 6, further comprising:
sending a position signal associated with the target position to a beam generator controller; and
controlling a beam generator to direct a beam at the target position.

8. The method of claim 1, wherein the non-linear correlation model comprises a two-dimensional model or a three-dimensional model.

9. An apparatus, comprising:
a data storage device to store a plurality of data points representative of a corresponding plurality of positions over time of an external marker, the data storage device to store a plurality of images of an internal target of the patient, the plurality of images corresponding in time to the plurality of data points; and
a processing device coupled to the data storage device, the processing device configured to:
develop a non-linear correlation model of a non-linear path of movement of the target based on the plurality of data points and the plurality of images to correlate a plurality of positions of the internal target with the plurality of positions of the external marker, wherein developing the non-linear correlation model comprises:
generate an inspiration approximation associated with the non-linear path of movement of the target over an inspiration interval of the non-linear path;
generate an expiration approximation associated with the non-linear path of movement of the target over an expiration interval of the non-linear path; and
generate one or more matching approximations to link the inspiration approximation and the expiration approximation.

10. The apparatus of claim 9, wherein the non-linear correlation model comprises a polynomial approximation of the non-linear path of movement of the target.

11. The apparatus of claim 9, wherein the non-linear correlation model comprises a multi-linear model having a plurality of linear approximations connected at a non-zero angle.

12. The apparatus of claim 9, wherein developing the non-linear correlation model comprises generating one or derivatives from the plurality of data points, the one or more derivatives comprising one or more directional indicators.

13. The apparatus of claim 9, wherein the inspiration approximation and the expiration approximation are derived from at least partially overlapping data sets.

14. The apparatus of claim 9, further comprising:
a beam generator controller operatively coupled with processing device, wherein the processing device is further configured to derive a target position of the target based on the non-linear correlation model and sending a position signal associated with the target position to the beam generator controller;
a beam generator operatively coupled with the beam generator controller to direct a beam at the target position.

15. A non-transitory machine readable storage medium having instructions thereon, which when executed by a processing device, cause the processing device to perform one or more operations comprising:
receiving a plurality of data points representative of a corresponding plurality of positions over time of an external marker associated with respiration of a patient;
receiving a plurality of images of an internal target of the patient, the plurality of images corresponding in time to the plurality of data points;
developing, using a processing device, a non-linear correlation model of a non-linear path of movement of the target based on the plurality of data points and the plurality of images to correlate a plurality of positions of the internal target with the plurality of positions of the external marker, wherein developing the non-linear correlation model comprises:
generating an inspiration approximation associated with the non-linear path of movement of the target over an inspiration interval of the non-linear path;
generating an expiration approximation associated with the non-linear path of movement of the target over an expiration interval of the non-linear path; and
generating one or more matching approximations to link the inspiration approximation and the expiration approximation.

16. The non-transitory machine readable storage medium of claim 15, wherein the non-linear correlation model comprises a polynomial approximation of the non-linear path of movement of the target.

17. The non-transitory machine readable storage medium of claim 15, wherein the non-linear correlation model comprises a multi-linear model having a plurality of linear approximations connected at a non-zero angle.

18. The non-transitory machine readable storage medium of claim 15, wherein developing the non-linear correlation model comprises generating one or derivatives from the plurality of data points, the one or more derivatives comprising one or more directional indicators.

19. The non-transitory machine readable storage medium of claim 15, wherein the inspiration approximation and the expiration approximation are derived from at least partially overlapping data sets.

20. The non-transitory machine readable storage medium of claim 15, wherein the one or more operations further comprise deriving a target position of the target based on the non-linear correlation model.

21. The non-transitory machine readable storage medium of claim 20, wherein the one or more operations further comprise:
sending a position signal associated with the target position to a beam generator controller; and
controlling a beam generator to direct a beam at the target position.

* * * * *